United States Patent
Takeuchi et al.

(10) Patent No.: US 10,499,691 B2
(45) Date of Patent: Dec. 10, 2019

(54) NON-COMBUSTION TYPE FLAVOR INHALER

(71) Applicant: JAPAN TOBACCO INC., Tokyo (JP)

(72) Inventors: Manabu Takeuchi, Tokyo (JP); Akihiko Suzuki, Tokyo (JP); Takuma Nakano, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 168 days.

(21) Appl. No.: 15/795,420

(22) Filed: Oct. 27, 2017

(65) Prior Publication Data

US 2018/0042308 A1 Feb. 15, 2018

Related U.S. Application Data

(63) Continuation of application No. PCT/JP2016/063473, filed on Apr. 28, 2016.

(30) Foreign Application Priority Data

Apr. 30, 2015 (WO) .................. PCT/JP2015/063042

(51) Int. Cl.
*A24F 47/00* (2006.01)
*H05B 3/44* (2006.01)

(52) U.S. Cl.
CPC .............. *A24F 47/008* (2013.01); *H05B 3/44* (2013.01)

(58) Field of Classification Search
CPC .................................................. A24F 47/008
See application file for complete search history.

(56) References Cited

U.S. PATENT DOCUMENTS

2007/0012327 A1 1/2007 Karles et al.
2016/0205998 A1* 7/2016 Matsumoto ........... A61M 15/06
2016/0206003 A1* 7/2016 Yamada ................ A24F 47/008
(Continued)

FOREIGN PATENT DOCUMENTS

CA 2925649 A1 4/2015
EP 2460423 A1 6/2012
(Continued)

OTHER PUBLICATIONS

Japanese Final Decision of Rejection for corresponding Japanese Application No. 2017-515629, dated Jan. 25, 2019, with English translation.

(Continued)

*Primary Examiner* — James Harvey
(74) *Attorney, Agent, or Firm* — Birch, Stewart, Kolasch & Birch, LLP

(57) ABSTRACT

A non-combustion type flavor inhaler includes a housing/outer wall having an airflow path continuing from an inlet/air introduction hole to an outlet/a suction hole. An atomizing part/heat source atomizes an aerosol source without burning and sensor outputs a value that changes according to a user's puff operation. A heat source control unit controls a power supply output to the atomizing part based on an absolute value of slope formed by two or more response values derived from a value output from the sensor such that an aerosol amount falls within a desired range. The aerosol amount is an amount of an aerosol to be atomized by the atomizing part in one energization to the atomizing part.

10 Claims, 16 Drawing Sheets

(56) References Cited

U.S. PATENT DOCUMENTS

Figure 1:
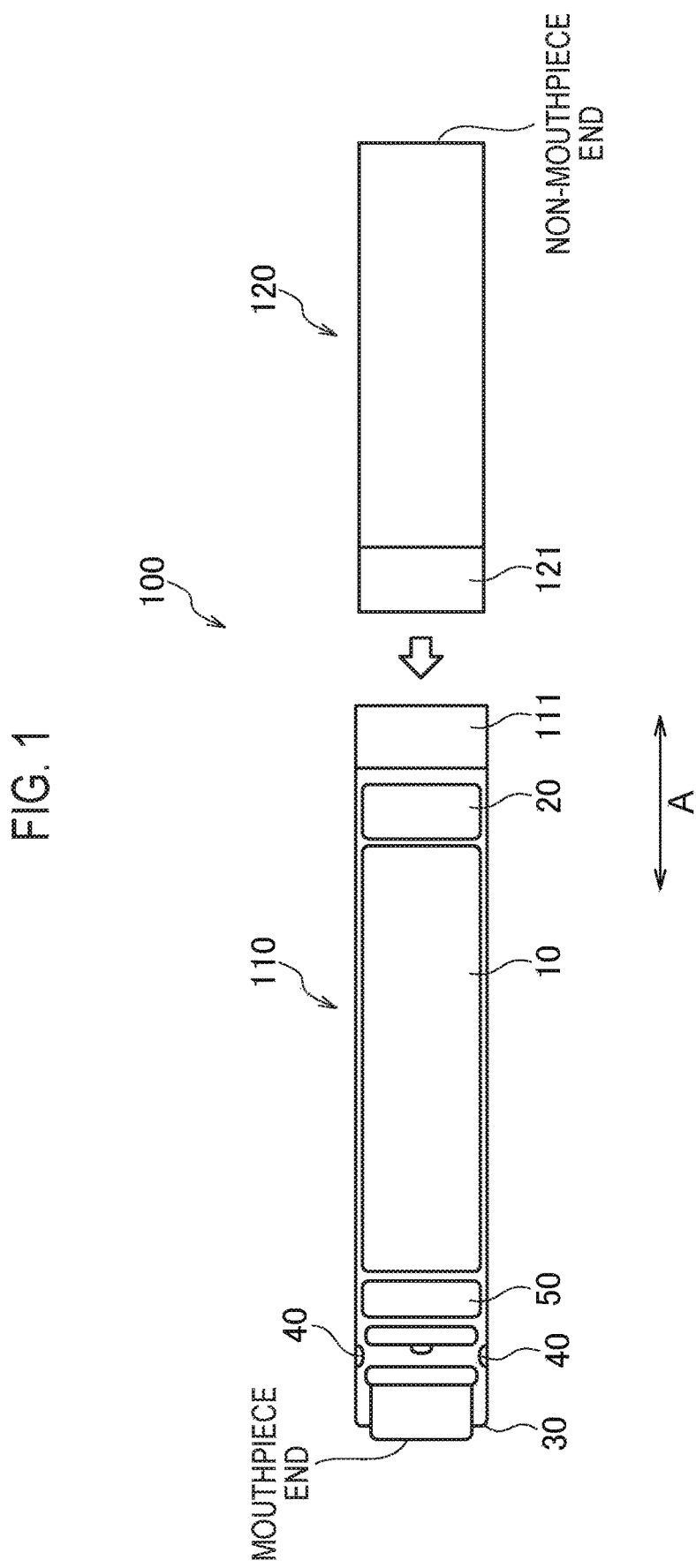

| | | | |
|---|---|---|---|
| 2016/0206005 A1* | 7/2016 | Yamada | A24F 47/008 |
| 2016/0331040 A1* | 11/2016 | Nakano | A61M 15/06 |
| 2017/0042251 A1* | 2/2017 | Yamada | A24F 47/00 |
| 2017/0042252 A1* | 2/2017 | Takeuchi | A24F 47/00 |
| 2018/0042308 A1* | 2/2018 | Takeuchi | A24F 47/00 |

FOREIGN PATENT DOCUMENTS

| | | |
|---|---|---|
| EP | 3138423 A1 | 3/2017 |
| JP | 2008-539717 A | 11/2008 |
| JP | 2010-104310 A | 5/2010 |
| TW | 201206357 A1 | 2/2012 |
| WO | WO 2007/123046 A1 | 11/2007 |
| WO | WO 2013/060781 A1 | 5/2013 |
| WO | WO 2013/060784 A2 | 5/2013 |
| WO | WO 2013/098398 A2 | 7/2013 |
| WO | WO 2013/116558 A1 | 8/2013 |
| WO | WO 2014/037259 A1 | 3/2014 |

OTHER PUBLICATIONS

Taiwanese Office Action and Search Report, dated Oct. 24, 2017, for Taiwanese Application No. 105113443, with an English translation of the Taiwanese Office Action.

Extended European Search Report, dated Nov. 15, 2018, for corresponding European Application No. 16786596.3.

Japanese Office Action, dated Aug. 7, 2018, for Japanese Application No. 2017-515629, with an English translation.

Taiwanese Office Action, dated Jul. 12, 2018, for Taiwanese Application No. 105113443, with an English translation.

International Search Report, issued in PCT/JP2016/063473, dated Aug. 2, 2016.

Taiwanese Office Action dated Apr. 25, 2019, for corresponding Taiwanese Patent Application No. 105113443, with English translation.

* cited by examiner

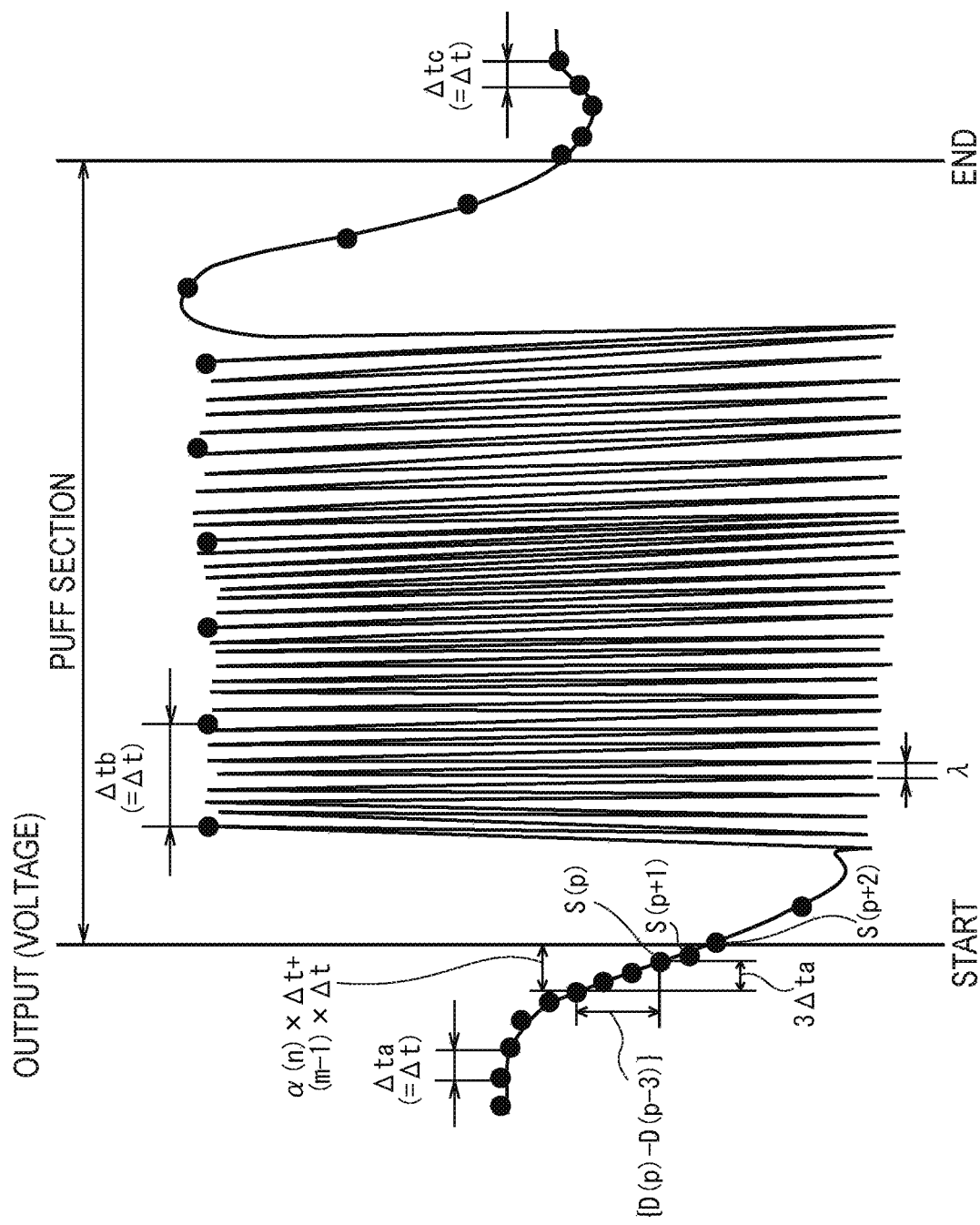

FIG. 6

| PUFF STATE | NON-PUFF STATE #1 | PUFF STATE #1 | NON-PUFF STATE #2 | PUFF STATE #2 | NON-PUFF STATE #3 | PUFF STATE #3 | NON-PUFF STATE #4 | PUFF STATE #4 |
|---|---|---|---|---|---|---|---|---|
| LIGHT-EMITTING MODE | LIGHT-EMITTING MODE #2-1 | LIGHT-EMITTING MODE #1 | LIGHT-EMITTING MODE #2-1 | LIGHT-EMITTING MODE #1 | LIGHT-EMITTING MODE #2-1 | LIGHT-EMITTING MODE #1 | LIGHT-EMITTING MODE #2-1 | LIGHT-EMITTING MODE #1 |

| PUFF STATE | NON-PUFF STATE #5 | PUFF STATE #5 | NON-PUFF STATE #6 | PUFF STATE #6 | NON-PUFF STATE #7 | PUFF STATE #7 | NON-PUFF STATE #8 | PUFF STATE #8 | NON-PUFF STATE #9 OR MORE | PUFF STATE #9 OR MORE |
|---|---|---|---|---|---|---|---|---|---|---|
| LIGHT-EMITTING MODE | LIGHT-EMITTING MODE #2-2 | LIGHT-EMITTING MODE #1 | LIGHT-EMITTING MODE #2-2 | LIGHT-EMITTING MODE #1 | LIGHT-EMITTING MODE #2-2 | LIGHT-EMITTING MODE #1 | LIGHT-EMITTING MODE #2-3 | LIGHT-EMITTING MODE #1 | EMISSION END MODE | LIGHT-EMITTING MODE #1 |

FIG. 7

| PUFF STATE | NON-PUFF STATE #1 | PUFF STATE #1 | NON-PUFF STATE #2 | PUFF STATE #2 | NON-PUFF STATE #3 | PUFF STATE #3 | NON-PUFF STATE #4 | PUFF STATE #4 |
|---|---|---|---|---|---|---|---|---|
| LIGHT-EMITTING MODE | LIGHT-EMITTING MODE #2-1 | LIGHT-EMITTING MODE #1-1 | LIGHT-EMITTING MODE #2-1 | LIGHT-EMITTING MODE #1-1 | LIGHT-EMITTING MODE #2-1 | LIGHT-EMITTING MODE #1-1 | LIGHT-EMITTING MODE #2-1 | LIGHT-EMITTING MODE #1-1 |

| PUFF STATE | NON-PUFF STATE #5 | PUFF STATE #5 | NON-PUFF STATE #6 | PUFF STATE #6 | NON-PUFF STATE #7 | PUFF STATE #7 | NON-PUFF STATE #8 | PUFF STATE #8 | NON-PUFF STATE #9 OR MORE | PUFF STATE #9 OR MORE |
|---|---|---|---|---|---|---|---|---|---|---|
| LIGHT-EMITTING MODE | LIGHT-EMITTING MODE #2-2 | LIGHT-EMITTING MODE #1-2 | LIGHT-EMITTING MODE #2-2 | LIGHT-EMITTING MODE #1-2 | LIGHT-EMITTING MODE #2-2 | LIGHT-EMITTING MODE #1-2 | LIGHT-EMITTING MODE #2-3 | LIGHT-EMITTING MODE #1-3 | EMISSION END MODE | LIGHT-EMITTING MODE #1-4 |

NON-COMBUSTION TYPE FLAVOR INHALER

CROSS REFERENCE TO RELATED APPLICATIONS

This application is a Continuation of PCT International Application No. PCT/JP2016/063473, filed on Apr. 28, 2016, which claims priority under 35 U.S.C. 119 (a) to Patent Application No. PCT/JP2015/063042, filed in Japan on Apr. 30, 2015, all of which are hereby expressly incorporated by reference into the present application.

TECHNICAL FIELD

The present invention relates to a non-combustion type flavor inhaler having an atomizing part that atomizes an aerosol source without burning.

BACKGROUND ART

A non-combustion type flavor inhaler for inhaling flavor without burning has been conventionally known. The non-combustion type flavor inhaler has an atomizing part that atomizes an aerosol source without burning (e.g., Patent Literature 1).

CITATION LIST

Patent Literature

Patent Literature 1: WO2013/116558

SUMMARY

A first feature is summarized as a non-combustion type flavor inhaler comprising: a housing having an airflow path continuing from an inlet to an outlet; an atomizing part that atomizes an aerosol source without burning; a sensor outputting a value that changes according to a user's puff operation; and a control unit that controls a power supply output to the atomizing part based on an absolute value of slope formed by two or more response values derived from a value output from the sensor such that an aerosol amount falls within a desired range, wherein the aerosol amount is an amount of an aerosol to be atomized by the atomizing part in one energization to the atomizing part.

A second feature is summarized as a non-combustion type flavor inhaler according to the first feature, wherein based on the absolute value of the slope, the control unit controls the magnitude of the power supply output to the atomizing part such that the aerosol amount falls within the desired range.

A third feature is summarized as a non-combustion type flavor inhaler according to the second feature, wherein the control unit increases the magnitude of the power supply output to the atomizing part as the absolute value of the slope is larger.

A fourth feature is summarized as a non-combustion type flavor inhaler according to the second feature, wherein the control unit uses a predetermined magnitude as the magnitude of the power supply output to the atomizing part when the absolute value of the slope is within a predetermined range, and the control unit increases the magnitude of the power supply output to the atomizing part to be larger than the predetermined magnitude when the absolute value of the slope is larger than the predetermined range.

A fifth feature is summarized as a non-combustion type flavor inhaler according to the third feature or the fourth feature, wherein an increase rate of the magnitude of the power supply output to the atomizing part is larger than 1 to 3 or less.

A sixth feature is summarized as a non-combustion type flavor inhaler according to the first feature or the fifth feature, wherein when a supply duration has elapsed since energization to the atomizing part has been started, the control unit stops the energization to the atomizing part such that the aerosol amount falls within the desired range, and the supply duration is equal to or less than an upper limit value of a standard puff period derived from statistics of a puff period of a user.

A seventh feature is summarized as a non-combustion type flavor inhaler according to the sixth feature, wherein the control unit reduces the supply duration as the absolute value of the slope is larger.

An eighth feature is summarized as a non-combustion type flavor inhaler according to the sixth feature, wherein the control unit uses a predetermined duration as the supply duration when the absolute value of the slope is within a predetermined range, and the control unit reduces the supply duration to be shorter than the predetermined duration when the absolute value of the slope is larger than the predetermined range.

A ninth feature is summarized as a non-combustion type flavor inhaler according to the seventh feature or the eighth feature, wherein a reduction rate of the supply duration is ⅓ or more to less than 1.

A tenth feature is summarized as a non-combustion type flavor inhaler according to any one of the sixth feature to the ninth feature, wherein in a first puff operation in which the absolute value of the slope is a first slope absolute value, the magnitude of the power supply output to the atomizing part is represented by $PX_1$, and the supply duration is represented by $TX_1$; in a second puff operation in which the absolute value of the slope is a second slope absolute value larger than the first slope absolute value, the magnitude of the power supply output to the atomizing part is represented by $PX_2$, and the supply duration is represented by $TX_2$; and the $TX_2$ is calculated according to an expression of $TX_2=(PX_1/PX_2)\times TX_1$.

An eleventh feature is summarized as a non-combustion type flavor inhaler according to any one of the first feature to the tenth feature, wherein the control unit reduces the magnitude of the power supply output to the atomizing part as an elapsed time from a start of energization to the atomizing part in one energization to the atomizing part is increased.

A twelfth feature is summarized as a non-combustion type flavor inhaler according to any one of the first feature to the eleventh feature, wherein when a supply duration has elapsed since energization to the atomizing part has been started, the control unit stops the energization to the atomizing part such that the aerosol amount falls within the desired range and the control unit determines the supply duration based on a learning result of required time of a user's puff operation.

In the above-described feature, a power supply output (hereinafter also referred to as a power supply amount) to the atomizing part can be expressed by, for example, $E=\{(D_2\times V)^2/R\}\times D_1 \times t$. Here, E is the power supply amount, V is an output voltage value, which is a value of a voltage applied to the atomizing part from the power source that accumulates electrical energy, and R is a resistance value of the atomizing part. Additionally, $D_1$ is a duty ratio (e.g., pulse width/1 cycle (here, 1 cycle=pulse width+pulse interval)), and $D_2$ is a correction coefficient of the output voltage value. Then, t is a time elapsed from a start of energization to the atomizing part. In a case where the duty is not controlled, it can be considered that $D_1$ is 1, and in a case where the output voltage value is not corrected, it can be considered that $D_2$ is 1.

In the above-described feature, magnitude of the power supply output to the atomizing part can be expressed by, for example, $P=\{(D_2 \times V)^2/R\} \times D_1$. Here, P is the magnitude of the power supply output to the atomizing part. Meanings of the other symbols are as described above. As described above, in the case where the duty is not controlled, it can be considered that $D_1$ is 1, and in the case where the output voltage value is not corrected, it can be considered that $D_2$ is 1.

In the above-described feature, when the sensor detects a start of a puff operation, the control unit starts energization to the atomizing part, and when the sensor detects an end of the puff operation, the control unit stops the energization to the atomizing part. However, when the supply duration has elapsed, the control unit stops the energization to the atomizing part even during the puff operation.

In the above-described feature, the control unit stores the above-mentioned $PX_1$ and $TX_1$ in advance, and the above-mentioned $PX_2$ is determined based on the second slope absolute value.

In the above-described feature, an increase rate of the magnitude of the power supply output to the atomizing part is an increase rate ($PX_2/PX_1$) of the magnitude of the power supply output of the second puff operation with respect to the first puff operation.

In the above-described feature, a reduction rate of the supply duration is a reduction rate ($TX_2/TX_1$) of a supply duration of the second puff operation with respect to the first puff operation.

In the above-described feature, the response value derived from the value output from the sensor may be the output value itself output from the sensor, or may be a value obtained by predetermined conversion of the output value. For example, the output value may be a value (e.g., a voltage value or a current value) indicating an environment (e.g., a pressure or a flow rate of an airflow path) that changes according to a user's puff operation, or may be a value (e.g., a flow rate value) obtained by predetermined conversion of the value. For example, the response value may be a value (e.g., a voltage value or a current value) indicating an environment that changes according to a user's puff operation, or may be a value (e.g., a flow rate value) obtained by predetermined conversion of the value.

In the above-described feature, the non-combustion type flavor inhaler includes a holder that holds an aerosol source, and the holder holds the aerosol source in an amount allowing aerosol to be inhaled over a plurality of puff operations.

BRIEF DESCRIPTION OF DRAWINGS

FIG. 1 is a view showing a non-combustion type flavor inhaler 100 according to a first embodiment.

FIG. 2 is a view showing an atomizing unit 120 according to the first embodiment.

FIG. 3 is a view showing a sensor 20 according to the first embodiment.

FIG. 4 is a block diagram showing a control circuit 50 according to the first embodiment.

FIG. 5 is a view for describing a detection of a puff duration according to the first embodiment.

FIG. 6 is a table showing an example of a light-emitting mode according to the first embodiment.

FIG. 7 is a table showing an example of a light-emitting mode according to the first embodiment.

FIG. 8 is a graph showing an example of control of magnitude of a power supply output in a puff operation series according to the first embodiment.

FIG. 9 is a graph showing an example of control of magnitude of a power supply output in a puff operation series according to the first embodiment.

FIG. 10 is a graph showing an example of control of magnitude of a power supply output per one puff operation according to the first embodiment.

FIG. 11 is a graph showing an example of control of magnitude of a power supply output per one puff operation according to the first embodiment.

FIG. 12 is a graph showing an example of control of magnitude of a power supply output in a puff operation series according to Modified Example 1 of the first embodiment.

FIG. 13 is a graph showing an example of control of a supply duration in a puff operation series according to Modified Example 2 of the first embodiment.

FIG. 14 is a graph for describing control of magnitude of a power supply output according to Modified Example 4 of the first embodiment.

FIG. 15 is a graph for describing control of magnitude of a power supply output according to Modified Example 5 of the first embodiment.

FIG. 16 is a graph for describing control of a power supply output according to Modified Example 5 of the first embodiment.

FIG. 17 is a graph for describing control of magnitude of a power supply output according to Modified Example 6 of the first embodiment.

FIG. 18 is a graph for describing control of magnitude of a power supply output according to Modified Example 6 of the first embodiment.

FIG. 19 is a graph for describing control of a power supply output according to Modified Example 7 of the first embodiment.

DESCRIPTION OF EMBODIMENTS

[Summary of Embodiments]

In the non-combustion type flavor inhaler mentioned in the background art, in a case where a mode of puff operation is different for each user, or in a case where a mode of puff operation is different for each puff operation by a same user, it has been difficult to appropriately and quickly control a total amount of an aerosol to be inhaled by a user for each puff operation.

In a non-combustion type flavor inhaler according to an embodiment includes: a housing having an airflow path continuing from an inlet to an outlet; an atomizing part that atomizes an aerosol source without burning; a sensor that outputs a value that changes according to a user's puff operation; and a control unit that controls a power supply output to the atomizing part such that an aerosol amount, which is an amount of an aerosol to be atomized by the atomizing part in one energization to the atomizing part, falls within a desired range, based on an absolute value of a slope (hereinafter referred to as an absolute value of slope or a slope absolute value) formed by two or more response values derived from a value output from the sensor.

In an embodiment, the control unit controls the power supply output to the atomizing part such that the aerosol amount falls within a desired range, based on the absolute value of slope. Namely, by estimating a mode of puff operation for each puff operation based on the absolute value of slope, it is possible to appropriately and quickly control the total amount of the aerosol to be inhaled by a user for each puff operation.

[First Embodiment]

(Non-Combustion Flavor Suction Apparatus)

Figure 2:
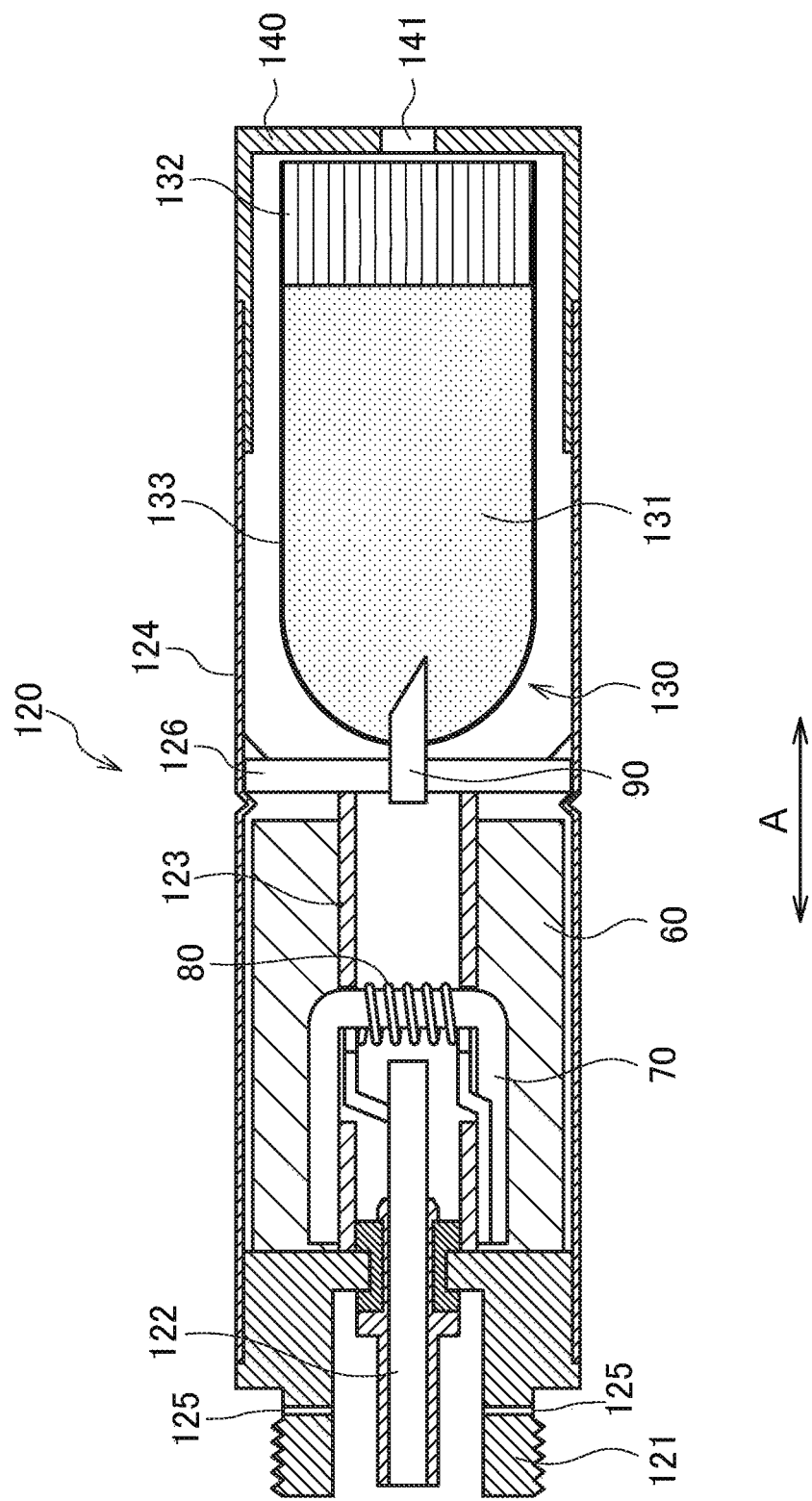

Hereinafter, a non-combustion type flavor inhaler according to a first embodiment will be described. FIG. 1 is a view showing a non-combustion type flavor inhaler 100 according to the first embodiment. FIG. 2 is a view showing an atomizing unit 120 according to the first embodiment.

In the first embodiment, the non-combustion type flavor inhaler 100 is a tool for inhaling flavor without burning, and has a shape extending along a predetermined direction A from a non-inhalation side toward an inhalation side. In the first embodiment, "inhalation side" may be considered to be synonymous with "downstream" of an aerosol flow, and "non-inhalation side" may be considered to be synonymous with "upstream" of the aerosol flow.

As shown in FIG. 1, the non-combustion type flavor inhaler 100 has an electrical unit 110 and the atomizing unit 120. The electrical unit 110 has a female connector 111 at a position adjacent to the atomizing unit 120, and the atomizing unit 120 has a male connector 121 at a position adjacent to the electrical unit 110. The female connector 111 has a spiral groove extending along a direction orthogonal to the predetermined direction A, and the male connector 121 has a spiral protrusion extending along the direction orthogonal to the predetermined direction A. By screwing the male connector 121 into the female connector 111, the atomizing unit 120 and the electrical unit 110 are connected to each other. The atomizing unit 120 is configured to be attachable/detachable to/from the electrical unit 110.

The electrical unit 110 has a power source 10, a sensor 20, a pushbutton 30, a light-emitting element 40, and a control circuit 50.

The power source 10 is a lithium-ion battery, for example. The power source 10 accumulates electrical energy for applying a voltage to each configuration of the non-combustion type flavor inhaler 100. For example, the power source 10 accumulates electrical energy for applying a voltage to the sensor 20, the light-emitting element 40, and the control circuit 50. Further, the power source 10 accumulates electric energy for applying a voltage to a heat source 80 described later.

The sensor 20 outputs a value (e.g., a voltage value or a current value) that changes in accordance with air inhaled from the non-inhalation side toward the inhalation side (i.e. user's puff operation). In the first embodiment, the sensor 20 has a capacitor, and outputs a value indicating electric capacity of the capacitor, which changes in accordance with air inhaled from the non-inhalation side toward the inhalation side (i.e. user's puff operation). Here, the value output by the sensor 20 is a voltage value. The sensor 20 is, for example, a condenser microphone sensor.

Figure 3:
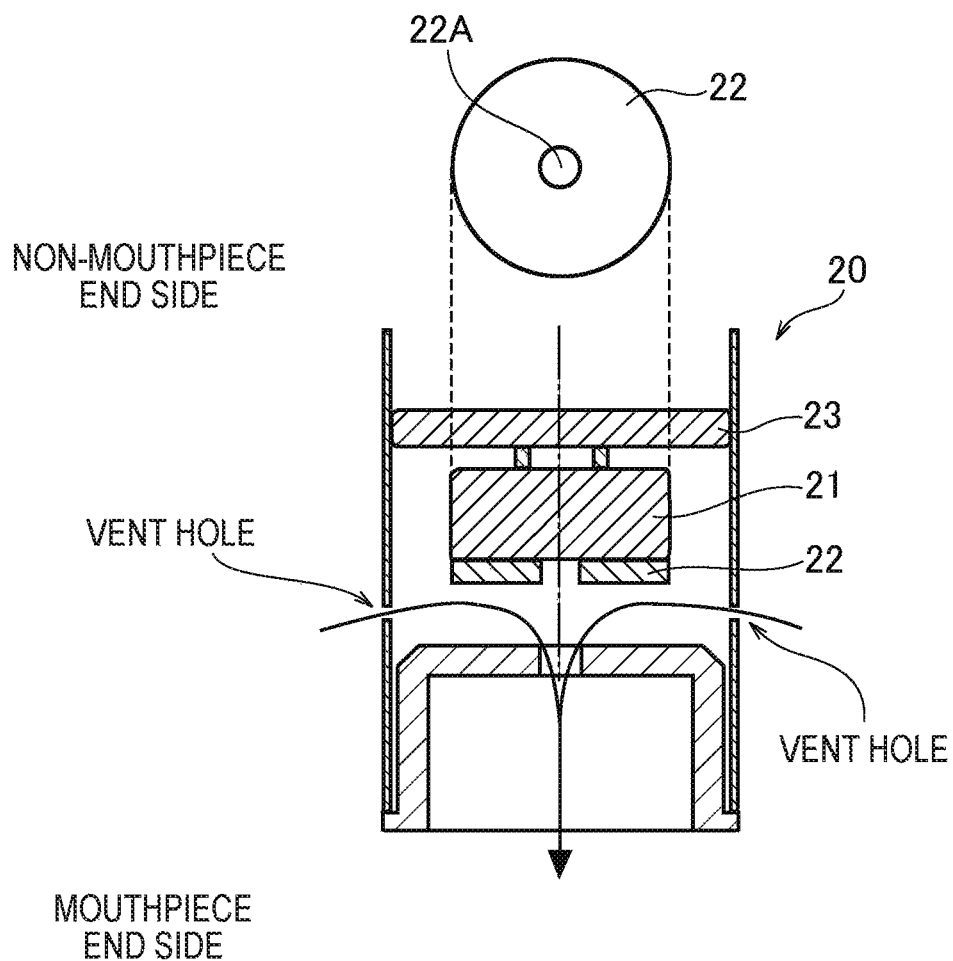

Specifically, as shown in FIG. 3, the sensor 20 has a sensor body 21, a cover 22, and a substrate 23. The sensor body 21 is configured by a capacitor, for example, and electric capacity of the sensor body 21 changes with vibration (pressure) generated by air inhaled from an air introduction hole 125 (i.e. air inhaled from the non-inhalation side toward the inhalation side). The cover 22 is provided on the inhalation side with respect to the sensor body 21, and has an opening 22A. Providing the cover 22 having the opening 22A allows the electric capacity of the sensor body 21 to be changed easily, and improves the response characteristic of the sensor body 21. The substrate 23 outputs a value (here, a voltage value) indicating the electric capacity of the sensor body 21 (capacitor).

In FIG. 3, the cover 22 covers only an inhalation-side end of the sensor body 21, but the first embodiment is not limited to this. For example, the cover 22 may cover a side surface of the sensor body 21 in addition to the inhalation-side end of the sensor body 21. Although FIG. 3 exemplifies a case where the air introduction hole 125 is provided on the inhalation side from the sensor 20, the first embodiment is not limited to this. For example, the air introduction hole 125 may be provided on the non-inhalation side from the sensor 20.

Returning to FIG. 1, the pushbutton 30 is configured to be pushed inward from outside of the non-combustion type flavor inhaler 100. In the first embodiment, the pushbutton 30 is provided at a non-inhalation end of the non-combustion type flavor inhaler 100, and configured to be pushed in a direction from the non-inhalation end toward an inhalation end (i.e. in a predetermined direction A). For example, when the pushbutton 30 is continuously pushed in for a predetermined number of times, the non-combustion type flavor inhaler 100 is powered on. It should be noted that the power source of the non-combustion type flavor inhaler 100 may be disconnected when a predetermined time elapses without puff operation after puff operation is performed.

The light-emitting element 40 is, for example, a light source such as an LED or an electric lamp. The light-emitting element 40 is provided on a sidewall extending along a predetermined direction. The light-emitting element 40 is preferably provided on a side wall near the non-inhalation end. This allows a user to visually recognize a light-emitting pattern of the light-emitting element 40 during a puff operation easily, as compared with a case where the light-emitting element is provided only on an end face of the non-inhalation end on an axis in the predetermined direction A. The light-emitting pattern of the light-emitting element 40 is a pattern to notify a user of a state of the non-combustion type flavor inhaler 100.

The control circuit 50 controls operation of the non-combustion type flavor inhaler 100. In particular, the control circuit 50 controls the light-emitting pattern of the light-emitting element 40, and controls a power supply output to the heat source 80.

The atomizing unit 120 has, as shown in FIG. 2, a holder 60, an absorber 70, the heat source 80, and a breaker 90. The atomizing unit 120 has a capsule unit 130 and an inhalation unit 140. Here, the atomizing unit 120 has the air introduction hole 125 to take outside air inside, an airflow path 122 that communicates with the electrical unit 110 (sensor 20) via the male connector 121, and a ceramic 123 arranged in a cylindrical shape. The atomizing unit 120 has a cylindrical outer wall 124 forming an outer shape of the atomizing unit 120. A space surrounded by the ceramic 123 forms an airflow path. The ceramic 123 contains alumina, for example, as a main component.

The holder 60 has a cylindrical shape, and holds an aerosol source that generates aerosol. The aerosol source is liquid such as propylene glycol or glycerin. The holder 60 is formed by a porous body impregnated with the aerosol source, for example. The porous body is a resin web, for example.

Further, in the first embodiment, the above-described ceramic 123 is arranged inside the holder 60, suppressing volatilization of the aerosol source held by the holder 60.

The absorber 70 is provided adjacent to the holder 60, and is formed by a material that absorbs the aerosol source from the holder 60. The absorber 70 is made of glass fiber, for example.

The heat source 80 heats the aerosol source without burning. In other words, the heat source 80 is an example of an atomizing part that atomizes the aerosol source without burning. For example, the heat source 80 is a heating wire wound around the absorber 70. The heat source 80 heats the aerosol source absorbed by the absorber 70.

In the first embodiment, as the heat source 80, a heating type component that atomizes the aerosol source by heating is exemplified. However, the atomizing part only has to have a function of atomizing the aerosol source, and may be an ultrasonic type component that atomizes the aerosol source by ultrasonic waves.

The breaker 90 is a member to break a part of a predetermined film 133 in a state where the capsule unit 130 is mounted. In the embodiment, the breaker 90 is held by a partition member 126 that partitions the atomizing unit 120 and the capsule unit 130. The partition member 126 is, for example, made of a polyacetal resin. The breaker 90 is a hollow cylindrical needle extending along the predetermined direction A, for example. By piercing a tip of the hollow needle into the predetermined film 133, a part of the predetermined film 133 is broken. Further, an inner space of the hollow needle forms an airflow path that pneumatically communicates the atomizing unit 120 with the capsule unit 130. Here, it is preferable that an inside of the hollow needle is provided with a mesh having a roughness of not allowing a material composing a tobacco source 131 to pass through. The roughness of the mesh is 80 meshes or more to 200 meshes or less, for example.

In such a case, the insertion depth of the hollow needle into the capsule unit 130 is preferably 1.0 mm or more to 5.0 mm or less, more preferably, 2.0 mm or more to 3.0 mm or less. This prevents breakage of portions except a desired portion of the predetermined film 133, enabling suppression of detachment of the tobacco source 131 filled in a space partitioned by the predetermined film 133 and a filter 132. Furthermore, since the detachment of the hollow needle from the space is suppressed, a proper airflow path to the filter 132 from the hollow needle can be preferably maintained.

In a vertical cross-section with respect to the predetermined direction A, a cross-sectional area of a vertical needle is preferably 2.0 mm$^2$ or more to 3.0 mm$^2$ or less. This prevents the tobacco source 131 from falling off the capsule unit 130 when the hollow needle is removed.

The tip of the hollow needle preferably has a slope of 30° or more to 45° or less with respect to the vertical direction to the predetermined direction A.

However, the embodiment is not limited to this. The breaker 90 may be a portion adjacent to the predetermined film 133 in a state where the capsule unit 130 is mounted. A part of the predetermined film 133 may be broken by pressure applied to such a portion by a user.

The capsule unit 130 is configured to be attachable/detachable to/from the main body unit. The capsule unit 130 has the tobacco source 131, the filter 132, and the predetermined film 133. The tobacco source 131 is filled in a space partitioned by the predetermined film 133 and the filter 132. Here, the main body unit is a unit that is configured by a portion other than the capsule unit 130. For example, the main body unit includes the electrical unit 110, the holder 60, the absorber 70, and the heat source 80 described above.

The tobacco source 131 is provided on the inhalation side from the holder 60 holding the aerosol source, and generates flavor to be inhaled by a user together with aerosol generated by the aerosol source. Here, it should be noted that the tobacco source 131 is composed of a solid material so as not to flow out of the space partitioned by the predetermined film 133 and the filter 132. As the tobacco source 131, it is possible to use shredded tobacco, a molded body of a granulated tobacco material, and a molded body formed into a sheet tobacco material. The tobacco source 131 may be given flavors such as menthol.

When the tobacco source 131 is composed of a tobacco material, since the tobacco material is apart from the heat source 80, it is possible to inhale the flavor without heating the tobacco material. In other words, it should be noted that inhalation of unwanted substance generated by heating the tobacco material is suppressed.

In the first embodiment, an amount of the tobacco source 131 filled in the space partitioned by the filter 132 and the predetermined film 133 is preferably 0.15 g/cc or more to 1.00 g/cc or less. A volume occupancy of the tobacco source 131 in the space partitioned by the filter 132 and the predetermined film 133 is preferably 50% or more to 100% or less. A volume of the space partitioned by the filter 132 and the predetermined film 133 is preferably 0.6 ml or more to 1.5 ml or less. This allows the tobacco source 131 to be contained to an extent enough to allow a user to taste flavor while maintaining an appropriate size of the capsule unit 130.

In a state where a part of the predetermined film 133 is broken by the breaker 90, and the atomizing unit 120 and the capsule unit 130 are communicated with each other, when air is inhaled from a tip portion (portion to be broken) of the capsule unit 130 to a terminal end of the filter 132 at a flow rate of 1050 cc/min, an airflow resistance (pressure loss) of the capsule unit 130 is preferably 10 mmAq or more to 100 mmAq or less as a whole, more preferably, 20 mmAq or more to 90 mmAq or less. Setting the airflow resistance of the tobacco source 131 to the above preferable range prevents the aerosol from being excessively filtered by the tobacco source 131, and allows efficient supply of flavor to a user. Moreover, since 1 mmAq corresponds to 9.80665 Pa, the airflow resistance can also be expressed by Pa.

The filter 132 is adjacent to the inhalation side with respect to the tobacco source 131, and is formed by a permeable material. The filter 132 is preferably an acetate filter, for example. The filter 132 preferably has roughness of not allowing a material composing the tobacco source 131 to pass through.

An airflow resistance of the filter 132 is preferably 5 mmAq or more to 20 mmAq or less. This allows the aerosol to efficiently pass through while efficiently absorbing a vapor component generated by the tobacco source 131, and allows an appropriate flavor to be supplied to a user. Further, an appropriate feeling of air resistance can be given to a user.

A ratio (mass ratio) between mass of the tobacco source 131 and mass of the filter 132 is preferably in a range of 3:1 to 20:1, more preferably, in a range of 4:1 to 6:1.

The predetermined film 133 is formed integrally with the filter 132, and is formed by an impermeable material. The predetermined film 133 covers a part of the outer surface of the tobacco source 131 except a portion adjacent to the filter 132. The predetermined film 133 includes at least one compound selected from a group consisting of gelatin, polypropylene, and polyethylene terephthalate. Gelatin, polypropylene, polyethylene, and polyethylene terephthalate are not permeable, and suitable for forming a thin film. Gelatin, polypropylene, polyethylene, and polyethylene terephthalate provide a sufficient resistance to moisture contained in the tobacco source 131. Polypropylene, polyethylene, and polyethylene terephthalate are especially excellent in a water resistance. Further, gelatin, polypropylene, and polyethylene have a base resistance, and are thus hardly degraded by a basic component even when the tobacco source 131 has a basic component.

A thickness of the predetermined film 133 is preferably 0.1 µm or more to 0.3 µm or less. This allows a part of the predetermined film 133 to be easily broken while maintaining a function of protecting the tobacco source 131 with the predetermined film 133.

As described above, while the predetermined film 133 is formed integrally with the filter 132, the predetermined film 133 is bonded to the filter 132 by paste or the like, for example. Alternatively, by setting an outer shape of the predetermined film 133 smaller than that of the filter 132 in a vertical direction with respect to the predetermined direction A, the filter 132 may be stuffed into the predetermined film 133, and the filter 132 may be fitted into the predetermined film 133 by a restoring force of the filter 132. Alternatively, the filter 132 may be provided with an engagement part to engage the predetermined film 133.

Here, a shape of the predetermined film 133 is not particularly limited, but preferably has a concave shape in the vertical cross-section with respect to the predetermined direction A. In such a case, after filling the tobacco source 131 inside the predetermined film 133 having the concave shape, an opening of the predetermined film 133 filled with the tobacco source 131 is closed by the filter 132.

When the predetermined film 133 has the concave shape in the vertical cross-section with respect to the predetermined direction A, a maximum sectional area (i.e. a cross-sectional area of an opening in which the filter 132 is fitted) of the sectional area of the space surrounded by the predetermined film 133, is preferably 25 mm$^2$ or more to 80 mm$^2$ or less, more preferably, 25 mm$^2$ or more to 55 mm$^2$ or less. In such a case, in the vertical cross-section with respect to the predetermined direction A, a cross-sectional area of the filter 132 is preferably 25 mm$^2$ or more to 55 mm$^2$ or less. A thickness of the filter 132 in the predetermined direction A is preferably 3.0 mm or more to 7.0 mm or less.

The inhalation unit 140 has a suction hole 141. The suction hole 141 is an opening to expose the filter 132. A user inhales flavor together with aerosol by inhaling aerosol through the suction hole 141.

In the first embodiment, the inhalation unit 140 is configured to be attachable/detachable to/from the outer wall 124 of the atomizing unit 120. For example, the inhalation unit 140 has a cup shape configured to be fitted to an inner surface of the outer wall 124. However, the embodiment is not limited to this. The inhalation unit 140 may be rotatably attached to the outer wall 124 with a hinge or the like.

In the first embodiment, the inhalation unit 140 is provided separately from the capsule unit 130. In other words, the inhalation unit 140 forms a part of the main body unit. However, the embodiment is not limited to this. The inhalation unit 140 may be provided integrally with the capsule unit 130. In such a case, it should be noted that the inhalation unit 140 forms a part of the capsule unit 130.

As described above, in the first embodiment, the non-combustion type flavor inhaler 100 has the outer wall 124 (housing) of the atomizing unit 120 having the airflow path 122 that continues from the air introduction hole 125 (inlet) to the suction hole 141 (outlet). In the first embodiment, the airflow path 122 is formed by the atomizing unit 120, but a mode of the airflow path 122 is not limited to this. The airflow path 122 may be formed by both the housing of the electrical unit 110 and the housing of the atomizing unit 120.

As described above, in the first embodiment, the non-combustion type flavor inhaler 100 includes the holder 60 that holds the aerosol source, and the holder 60 holds the aerosol source in an amount allowing aerosol to be inhaled over a plurality of puff operations.

(Control Circuit)

Figure 4:
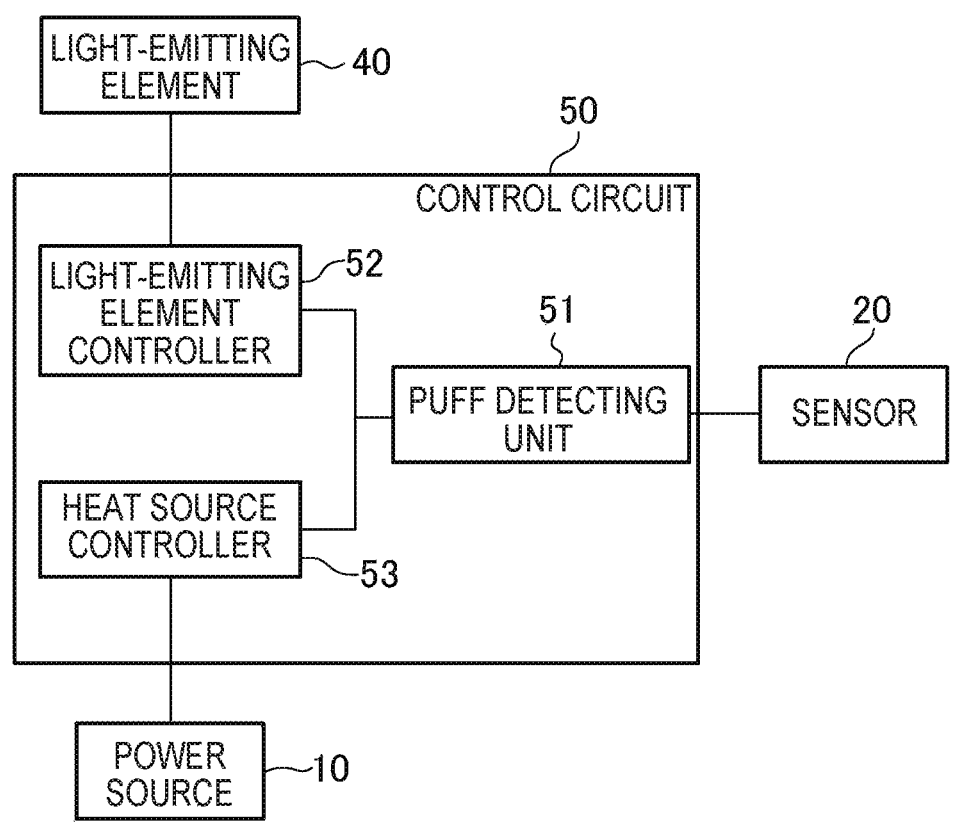

Hereinafter, a control circuit according to the first embodiment will be described. FIG. 4 is a block diagram showing the control circuit 50 according to the first embodiment.

As shown in FIG. 4, the control circuit 50 has a puff detection unit 51, a light-emitting element control unit 52, and a heat source control unit 53.

The puff detection unit 51 is connected to the sensor 20 that outputs a value that changes in accordance with air inhaled from the non-inhalation side toward the inhalation side. The puff detection unit 51 detects a puff state based on the detection results of the sensor 20 (e.g., a negative pressure in the non-combustion type flavor inhaler 100). Specifically, the puff detection unit 51 detects a puff state (puff duration) in which an aerosol is inhaled, and a non-puff state (non-puff duration) in which an aerosol is not inhaled. This allows the puff detection unit 51 to specify a number of puff operations for inhaling aerosol. Further, the puff detection unit 51 can detect required time per one puff operation for inhaling aerosol.

In the first embodiment, the puff detection unit 51 detects a start or end of the puff duration based on the slope formed by two or more response values derived from the output value output from the sensor 20. Here, the response value is the output value itself output from the sensor 20, and the output value is a voltage value indicating the electric capacity of the capacitor.

Specifically, the puff detection unit 51 detects the start or end of the puff duration, when the slope formed by two or more output values output from the sensor 20 has a predetermined sign (here, negative), and the absolute value of slope having the predetermined sign (here, negative) is larger than a predetermined value. In other words, the puff detection unit 51 detects the start of the puff duration when the above-described conditions are satisfied before the detection of the start of the puff duration. On the other hand, after detecting the start of the puff duration, the puff detection unit 51 detects the end of the puff duration when the above-described conditions are satisfied.

Here, the condition (predetermined value) used for the start of the puff duration may be same as the condition (predetermined value) used for the end of the puff duration, or may be different. Moreover, the end determination of the puff duration is preferably performed after a predetermined period (e.g., 200 msec to 500 msec) has elapsed since the start of the puff duration has been detected. This prevents erroneous detection of the end of the puff duration immediately after detection of the start of the puff duration.

Specifically, as shown in FIG. 5, the puff detection unit 51 monitors the output value output from the sensor 20 at a sampling period ($\Delta t$). It should be noted that, in FIG. 5, the voltage value is exemplified as the output value output from the sensor 20. A sampling period ($\Delta ta$) for monitoring the output value output from the sensor 20 before detection of the start of the puff duration is shorter than a sampling period ($\Delta tb$) for monitoring the output value output from the sensor 20 after detection of the start of the puff duration. A sampling period (Δtc) for monitoring the output value output from the sensor 20 after detection of the end of the puff duration is shorter than the sampling period (Δtb) for monitoring the output value output from the sensor 20 before detection of the end of the puff duration.

Note that the sampling period (Δta) for monitoring the output value output from the sensor 20 before detection of the start of the puff duration is similar to the sampling period (Δtc) for monitoring the output value output from the sensor 20 after detection of the end of the puff duration. Additionally, the sampling period (Δtb) for monitoring the output value output from the sensor 20 after detection of the start of the puff duration is similar to the sampling period (Δtb) for monitoring the output value output from the sensor 20 before detection of the end of the puff duration. In other words, the sampling period (Δta or Δtc) for monitoring the output value output from the sensor 20 outside the puff duration is shorter than the sampling period (Δtb) for monitoring the output value output from the sensor 20 within the puff duration. The sampling period (Δta or Δtc) for monitoring the output value output from the sensor 20 outside the puff duration is 1 msec, for example, and the sampling period (Δtb) for monitoring the output value output from the sensor 20 within the puff duration is 10 msec, for example.

Hereinafter, each symbol represents the following contents. The symbol Δt represents a period for monitoring the output value output from the sensor 20, D(n) represents the output value output from the sensor 20 at time t(n), α(n) represents a positive integer, and S(n) represents a slope formed by the output value output from the sensor 20 at time t(n). Note that n represents a number of calculation times of S(n). Additionally, α(n) may be a constant value (e.g., 3), and may change at each calculation of S(n).

Under such a premise, the puff detection unit 51 may calculate a slope formed by an output value output from the sensor 20, based on $S(n)=\{D(n)-D(n-\alpha(n)\times\Delta t)\}/(\alpha(n)\times\Delta t)$. It should be noted that "D (n−α(n)×Δt)" represents the output value monitored before time t(n) by "α(n)×Δt".

In such a case, before the detection of the start of the puff duration, the puff detection unit 51 detects the start of the puff duration when, for consecutive m times (m is an integer of 2 or more) of S(n), a condition that every S(n) is a value of a predetermined sign (here, negative) and the absolute value of every S(n) is larger than a first value described later is satisfied. Here, it should be noted that the sampling period (Δt) used for detecting the start of the puff duration is Δta (or Δtc). On the other hand, after detection of the start of the puff duration, the puff detection unit 51 detects the end of the puff duration when, for consecutive m times of S(n), a condition that every S(n) is a value of a predetermined sign (here, negative) and the absolute value of every S(n) is larger than the first value is satisfied. Here, it should be noted that the sampling period (Δt) used for detecting the end of the puff duration is Δtb (>Δta or Δtc).

For example, a case will be described where the start of the puff duration is detected when α(n)=3 and m=3, with reference to FIG. 5. In such a case, since all of S(p), S(p+1), and S(p+2) are negative values, and all the absolute values of S(p), S(p+1), and S(p+2) are larger than the first value, the start of the puff duration is detected at time p+2. For describing a calculation method of S(n) by exemplifying time p, S(p) is calculated by $S(p)=\{D(p)-D(p-3)/3\Delta t\}$.

It should be noted that the first value is a predetermined value that has been set in advance, and may be appropriately set depending on the type of the sensor 20 or the like. Further, a cycle in which the puff detection unit 51 calculates S(n) may be same as the sampling period (Δt), or may differ from the sampling period (Δt). The cycle in which the puff detection unit 51 calculates S(n) is preferably an integral multiple of the sampling period (Δt).

The sampling periods (Δt) and a calculation cycle of S(n) can be appropriately set. The sampling period (Δt) and the calculation cycle of S(n) are preferably synchronized, but they may not be synchronized. Further, a cycle in which the sensor 20 outputs the output value can also be appropriately set. Moreover, the sensor 20 may repeat ON/OFF in synchronization with the sampling period (Δt) and the calculation cycle of S(n), or may always be ON.

In the first embodiment, the sampling period (e.g., 5 msec) of the output value that is referred to in determining the start or end of the puff duration is preferably longer than the predetermined time. Specifically, as shown in FIG. 5, the sampling period of the output value that is referred to in determining the start or end of the puff duration is represented by α(n)×Δt+(m−1)×Δt. It is preferable that, under a premise that output values that vary in the puff duration are acquired discretely on a time axis, a continuous approximation function is derived from a plot of discretely acquired output values, and the predetermined time is longer than ½ of an average value of a wavelength (λ shown in FIG. 5) of a frequency of a waveform derived from the approximation function. Thus, setting a lower limit to the sampling period of the output value that is referred to in determining the start or end of the puff duration prevents accidental satisfaction of the above-described conditions due to an event different from the user's puff operation (e.g., vibration of human voice) before the detection of the start of the puff duration, improving accuracy of detecting the start of the puff duration. Even after detection of the start of the puff duration, accidental satisfaction of the above-described conditions before an actual end of the puff operation by a user is prevented, improving accuracy of detecting the end of the puff duration.

In the first embodiment, for one S(n) out of consecutive m times of S(n), the puff detection unit 51 preferably detects the start or end of the puff duration when a condition that the absolute value of S(n) is smaller than a second value is satisfied. The second value is a value sufficiently larger than the first value, and is preferably an average value of a slope (absolute value) formed by two or more output values that vary in the puff duration. In other words, for all consecutive m times of S(n), the puff detection unit 51 does not detect the start or end of the puff duration when S(n) is a value of a predetermined sign (here, negative) and the absolute value of S(n) is equal to or larger than the second value. Whereas, for consecutive m times of S(n), the puff detection unit 51 detects the start or end of the puff duration if a condition that every S(n) is larger than the first value is satisfied, and a condition that the absolute value of at least one S(n) is smaller than the second value is satisfied. This prevents erroneous detection of the start or end of the puff duration even when an electric capacity of the sensor 20 suddenly changes due to an event different from the puff operation. The event different from the puff operation is, for example, in a case where the non-combustion type flavor inhaler 100 is placed on a desk, an event that the electric capacity of the sensor 20 changes due to vibration on the desk, or an event that a user blows in instead of inhaling from an inhalation portion of the non-combustion type flavor inhaler 100, or the like.

In the first embodiment, the sampling period of the output value that is referred to in determining the start or end of the puff duration is α(n)×Δt+(m−1)×Δt. Namely, the sampling periods of the output values that are referred to in calculation of consecutive two times of S(n) out of m times of S(n) are partially overlapped each other, and α(n) is 2 or more. Consequently, as compared with a case where the sampling periods of the output values that are referred to in calculation of consecutive two times of S(n) are not overlapped, namely, as compared with a case where the sampling period of the output value that is referred to in determining the start or end of the puff duration is α(n)×Δt×m, the sampling period (α(n)×Δt+(m−1)×Δt) of the output value that is referred to in determining the start or end of the puff duration is short, so that the start of the puff duration can be quickly detected, improving accuracy of detecting the start of the puff duration. Furthermore, as compared with a case where α(n) is 1, fine fluctuation of the output value is not detected as the start of the puff duration, which can prevent erroneous detection of the puff duration.

The light-emitting element control unit 52 is connected to the light-emitting element 40 and the puff detection unit 51, and controls the light-emitting element 40. Specifically, the light-emitting element control unit 52 controls the light-emitting element 40 in a first light-emitting mode, in the puff state where the aerosol is inhaled. On the other hand, the light-emitting element control unit 52 controls the light-emitting element 40 in a second light-emitting mode, which is different from the first light-emitting mode, in the non-puff state where the aerosol is not inhaled.

Here, the light-emitting mode is defined by combination of parameters such as the amount of light of the light-emitting element 40, a number of the light-emitting element 40 in a lighting state, a color of the light-emitting element 40, and a cycle of repeating of turning on the light-emitting element 40 and turning off the light-emitting element 40. A different light-emitting mode means a light-emitting mode in which any of the above-described parameters is different.

In the first embodiment, the second light-emitting mode changes according to the number of puff operations for inhaling aerosol. The first light-emitting mode may be changed in accordance with the number of puff operations for inhaling aerosol, or may be constant without depending on the number of puff operations for inhaling aerosol.

For example, the first light-emitting mode is such a mode of lighting a red light-emitting element 40 to simulate a use feeling of a general cigarette that generates an aerosol with burning. The first light-emitting mode is preferably such a mode of continuously lighting the light-emitting element 40. Alternatively, the first light-emitting mode may be a mode of repeating turning on the light-emitting element 40 and turning off the light-emitting element 40 at a first cycle.

For example, the second light-emitting mode is such a mode of lighting a blue light-emitting element 40 to notify a user that the aerosol source is not heated. The second light-emitting mode may be a mode of repeating turning on the light-emitting element 40 and turning off the light-emitting element 40 at a second cycle longer than the first cycle.

As described above, the second light-emitting mode changes according to the number of puff operations for inhaling aerosol.

For example, the second light-emitting mode may be a mode of increasing the number of the light-emitting elements 40 to be controlled, along with an increase in the number of puff operations. For example, the light-emitting element control unit 52 controls one light-emitting element 40 in the second light-emitting mode in a first puff operation, and controls two light-emitting elements 40 in the second light-emitting mode in a second puff operation. Alternatively, the light-emitting element control unit 52 controls the n pieces of light-emitting element 40 in the second light-emitting mode in the first puff operation, and controls the n−1 pieces of light-emitting element 40 in the second light-emitting mode in the second puff operation.

Alternatively, the second light-emitting mode may be a light-emitting mode of increasing or decreasing light quantity of the light-emitting element 40 along with an increase in the number of puff operations. Alternatively, the second light-emitting mode may be a light-emitting mode of changing the color of the light-emitting element 40 along with an increase in the number of puff operations.

Even in the case that the first light-emitting mode changes depending on the number of puff operations, the concept of the change of the first light-emitting mode is basically same as the change of the second light-emitting mode.

In the first embodiment, when the number of puff operations for inhaling aerosol reaches a predetermined number (e.g., eight times), the light-emitting element control unit 52 terminates the control that is in accordance with the first light-emitting mode and the second light-emitting mode, and controls the light-emitting element 40 in an ending light-emitting mode.

The ending light-emitting mode may be a mode to notify a user of a timing to end the puff operation, and is preferably different from the first light-emitting mode and the second light-emitting mode. For example, the ending light-emitting mode is such a mode in which the amount of light of the light-emitting element 40 is smaller than that of the first light-emitting mode and the second light-emitting mode, and the amount of light of the light-emitting element 40 is gradually decreased.

The heat source control unit 53 is connected to the power source 10, and controls a power supply output (hereinafter also referred to as a power supply amount) from the power source 10 to the heat source 80 (atomizing part). Note that the power supply amount is a multiplication result of an elapsed time from the start of energization to the heat source 80 and the magnitude of the power supply output, and is a value that is controlled with the time and the magnitude of the power supply output.

In other words, the power supply amount can be expressed by, for example, $E=\{(D_2 \times V)^2/R\} \times D_1 \times t$. Here, E is the power supply amount, V is the output voltage value, which is a value of the voltage applied from the power source 10 to the heat source 80, and R is the resistance value of the heat source 80. Additionally, $D_1$ is a duty ratio, and $D_2$ is a correction coefficient of the output voltage value. Then, t is a time elapsed from the start of energization to the heat source 80. In a case where the duty is not controlled, it can be considered that $D_1$ is 1, and in a case where the output voltage value is not corrected, it can be considered that $D_2$ is 1. In a case where the output voltage value is corrected, the heat source control unit 53 controls the voltage applied to the heat source 80 from the power source 10 by controlling a DC-DC converter or the like that is provided along with the power source 10.

Here, in a case where a voltage is continuously applied to the heat source 80 (atomizing part), the magnitude of the power supply output is controlled by a value of the voltage applied to the heat source 80 (atomizing part). On the other hand, in a case where a voltage is intermittently applied to the heat source 80 (atomizing part) (duty control), the magnitude of the power supply output is controlled by a value of the voltage applied to the heat source 80 (atomizing part) and the duty ratio.

In other words, the magnitude of the power supply output to the heat source 80 can be expressed by, for example, $P=\{(D_2 \times V)^2/R\} \times D_1$. Here, P is the magnitude of the power supply output to the heat source 80. Meanings of the other symbols are as described above. As described above, in the case where the duty is not controlled, it can be considered that $D_1$ is 1, and in the case where the output voltage value is not corrected, it can be considered that $D_2$ is 1.

Firstly, the heat source control unit 53 increases the magnitude of the power supply output to the heat source 80 (atomizing part) stepwise from the magnitude of a reference power supply output along with an increase in the number of puff operations for inhaling aerosol. This makes it possible to simulate a use feeling of a general cigarette that generates an aerosol with burning.

Here, when a puff operation is performed after the number of puff operations exceeds a predetermined number, the heat source control unit 53 may use magnitude of a power supply output smaller than the magnitude of the reference power supply output as the magnitude of the power supply output to the heat source 80. Thus, a user can inhale a little amount of aerosol even at the timing to end the puff operation, increasing the user's satisfaction.

When a predetermined time elapses after the number of puff operations exceeds a predetermined number, the heat source control unit 53 turns off the power source of the non-combustion type flavor inhaler 100. This suppresses power waste of the non-combustion type flavor inhaler 100 due to forgetting to turn off the power source of the non-combustion type flavor inhaler 100.

Here, the heat source control unit 53 may use the magnitude of the power supply output smaller than the magnitude of the reference power supply output as the magnitude of the power supply output to the heat source 80 by combining the above-described operations after the number of puff operations exceeds a predetermined number, and may turn off the power source of the non-combustion type flavor inhaler 100 when a predetermined time elapses after the number of puff operations exceeds the predetermined number.

The heat source control unit 53 preferably increases a gradient of the magnitude of the power supply output to the heat source 80 along with an increase in the number of puff operations for inhaling aerosol. Here, the gradient of the magnitude of power supply output is defined by the number of puff operations in which a constant magnitude of the power supply output is maintained, and by an increase width in which the magnitude of the power supply output increases. In other words, along with an increase in the number of puff operations, the number of puff operations, in which the constant magnitude of the power supply output is maintained, is decreased. Alternatively, along with an increase in the number of puff operations, the increase width, in which the magnitude of the power supply output increases, is increased. Alternatively, along with an increase in the number of puff operations, the number of puff operations, in which the constant power supply output is maintained, is decreased, and the increase width, in which the magnitude of the power supply output increases, is increased.

Furthermore, the heat source control unit 53 may control a first mode that uses magnitude of a first reference power supply output as the magnitude of the reference power supply output, and a second mode that uses magnitude of a second reference power supply output, which is larger than the magnitude of the first reference power supply output, as the magnitude of the reference power supply output. As the magnitude of the reference power supply output, magnitude of a reference supply output of three or more steps may be prepared. In such a case, the magnitude of the reference power supply output may be switched by operating the pushbutton 30. For example, the first mode may be selected by pressing the pushbutton 30 once, and the second mode may be selected by pressing the pushbutton 30 twice. The pushbutton 30 may also be replaced with a touch sensor. The non-combustion type flavor inhaler 100 may be powered on by these operations. In other words, by one operation of the pushbutton 30, the power source may be turned on, and the magnitude of the reference power supply output may be switched. The operation of turning on the power source by operation of the pushbutton 30 may also be separated from the operation of switching the magnitude of the reference power supply output.

Secondly, the heat source control unit 53 controls a standard mode that is applied to a user whose required time per one puff operation for inhaling aerosol is within a standard required time duration, and a reduced mode that is applied to a user whose required time per one puff operation for inhaling aerosol is shorter than the standard required time duration. Here, the standard required time duration means a time duration in which a supply amount of aerosol (total particulate matter (TPM) amount) is particularly well balanced.

Specifically, in one puff operation in the standard mode, the heat source control unit 53 uses the magnitude of the standard power supply output as the magnitude of the power supply output to the heat source 80 in a duration until a first duration elapses, and uses magnitude of a power supply output smaller than the magnitude of the standard power supply output as the magnitude of the power supply output to the heat source 80 in a duration after the first duration has elapsed. It should be noted that the heat source control unit 53 may immediately set the magnitude of the power supply output to the heat source 80 to zero in the duration after the first duration has elapsed, and may gradually decrease the magnitude of the power supply output to the heat source 80.

Here, the first duration is preferably same as an end timing of the standard required time duration described above. However, the first duration may be longer than the end timing of the standard required time within a range allowing the balance of the supply amount of aerosol (TPM amount).

Whereas, in one puff operation in the reduced mode, the heat source control unit 53 uses magnitude of a first power supply output larger than the magnitude of the standard power supply output as the magnitude of the power supply output to the heat source 80 in the duration until a second duration elapses, uses magnitude of the second power supply output smaller than the magnitude of the first power supply output as the magnitude of the power supply output to the heat source 80 in the duration until a third duration elapses after the second duration, and uses magnitude of a power supply output smaller than the magnitude of the second power supply output as the magnitude of the power supply output to the heat source 80 in a duration after the third duration has elapsed. It should be noted that the heat source control unit 53 may immediately set the magnitude of the power supply output to the heat source 80 to zero in a duration after the third duration has elapsed, and may gradually decrease the magnitude of the power supply output to the heat source 80.

Here, the second duration is preferably shorter than a start timing of the standard required time duration described above. The second duration may be included in the standard required time duration, or may be longer than the end timing of the standard required time duration. The third duration is preferably same as the end timing of the standard required time duration described above. However, the third duration may be longer than the end timing of the standard required time within a range allowing the balance of the supply amount of aerosol (TPM amount).

The magnitude of the second power supply output smaller than the magnitude of the first power supply output may be same as the magnitude of the standard power supply output described above. However, the magnitude of the second power supply output may be larger than the magnitude of the standard power supply output, or may be smaller than the magnitude of the standard power supply output.

As described above, the heat source control unit 53 increases the magnitude of the power supply output to the heat source 80 stepwise from the magnitude of the reference power supply output along with an increase in the number of puff operations. In other words, it should be noted that the magnitude of the standard power supply output per one puff operation increases along with an increase in the number of puff operations.

The heat source control unit 53 may set the standard mode or the reduced mode according to learning of a user's puff operation. In particular, when a time required per one puff operation stored by learning is within the standard required time duration, the heat source control unit 53 sets the standard mode. When the time required per one puff operation stored by the learning is shorter than the standard required time duration, the heat source control unit 53 sets the reduced mode.

In the first embodiment, the atomizing unit 120 is attachable/detachable to/from the electrical unit 110. The capsule unit 130 is attachable/detachable to/from the main body unit including the electrical unit 110. In other words, the electrical unit 110 can be reused over multiple puff operation series. The puff operation series means a series of behaviors to repeat a predetermined number of puff operations. Therefore, by learning the required time per one puff operation in a first puff operation series, the standard mode or the reduced mode may be set in a second and subsequent puff operation series. Alternatively, in one puff operation series, by learning the required time per one puff operation in first n times of puff operations, the standard mode or the reduced mode may be set for the puff operation of the n+1th (or, n+2th) and subsequent puff operations.

Alternatively, the heat source control unit 53 may set the standard mode or the reduced mode according to an operation of a user. In such a case, a switch that switches the standard mode and the reduced mode is provided in the non-combustion type flavor inhaler 100. It may also be permitted to switch the standard mode and the reduced mode in one puff operation series. Alternatively, a mode initially set may be fixedly applied without permitting switching of the standard mode and the reduced mode in one puff operation series.

(Light-Emitting Mode)

Hereinafter, an example of the light-emitting mode according to the first embodiment will be described. FIGS. 6 and 7 are tables showing an example of the light-emitting mode according to the first embodiment. FIGS. 6 and 7 exemplify a case where a user should finish a puff operation series in principle when the number of puff operations reaches eight times (predetermined number of times).

Firstly, a first example of the light-emitting mode will be described with reference to FIG. 6. As shown in FIG. 6, a first light-emitting pattern in the puff state is constant without depending on the number of puff operations. On the other hand, a second light-emitting pattern in the non-puff state changes depending on the number of puff operations.

For example, as shown in FIG. 6, in non-puff states #1 to #4, light-emitting mode #2-1 is used as the second light-emitting mode. In non-puff states #5 to #7, light-emitting mode #2-2 is used as the second light-emitting mode. In non-puff state #8, light-emitting mode #2-3 is used as the second light-emitting mode. In the 9th and subsequent non-puff states, the above-described ending light-emitting mode is used.

On the other hand, in puff states #1 to #8, light-emitting mode #1 is used as the first light-emitting mode. Even in the 9th and subsequent puff states, light-emitting mode #1 may be used as the first light-emitting mode, or a light-emitting mode different from the first light-emitting mode and the second light-emitting mode may be used to indicate that the puff operation exceeds eight times (predetermined number of times).

Light-emitting modes #1, #2-1, #2-2, and #2-3, and the ending light-emitting mode are different light-emitting modes from each other. As described above, the light-emitting mode is defined by combination of parameters such as the amount of light of the light-emitting element 40, a number of the light-emitting element 40 in a lighting state, a color of the light-emitting element 40, and a cycle of repeating of turning on the light-emitting element 40 and turning off the light-emitting element 40. A different light-emitting mode means a light-emitting mode in which any of the above-described parameters is different.

For example, light-emitting mode #1 is preferably such a mode for generating image of burning in order to simulate a use feeling of a general cigarette that generates an aerosol with burning. It is preferable that light-emitting mode #2-1 is such a mode for generating image of the beginning of a puff operation series, light-emitting mode #2-2 is such a mode for generating image of the middle of the puff operation series, and light-emitting mode #2-3 is such a mode for generating image of the end of the puff operation series. The ending light-emitting mode is preferably such a mode to notify a user of a timing to end the puff operation.

Secondly, a first example of the light-emitting mode will be described with reference to FIG. 7. As shown in FIG. 7, both the first light-emitting pattern in the puff state and the second light-emitting pattern in the non-puff state are changed in accordance with the number of puff operations.

For example, as shown in FIG. 7, in the non-puff state, like the case shown in FIG. 6, the light-emitting modes #2-1, #2-2, and #2-3 are used as the second light-emitting mode.

On the other hand, in puff states #1 to #4, light-emitting mode #1-1 is used as the first light-emitting mode. In puff states #5 to #7, light-emitting mode #1-2 is used as the first light-emitting mode. In puff state #8, light-emitting mode #1-3 is used as the first light-emitting mode. In the 9th and subsequent puff states, light-emitting mode #1-4 is used.

It is preferable that light-emitting mode #1-1 is such a mode for generating image of the beginning of a puff operation series, light-emitting mode #1-2 is such a mode for generating image of the middle of the puff operation series, and light-emitting mode #1-3 is such a mode for generating image of the end of the puff operation series. Light-emitting mode #1-4 is, like the ending light-emitting mode, preferably such a mode to notify a user of a timing to end the puff operation.

As shown in FIGS. 6 and 7, the first embodiment has exemplified a case where the light-emitting mode in non-puff state #1 (i.e. the non-puff state immediately after turning on the power source of the non-combustion type flavor inhaler 100) is the second light-emitting mode (light-emitting mode #2-1). However, the embodiment is not limited to this. The light-emitting mode in non-puff state #1 may be a starting light-emitting mode different from the second light-emitting mode. The starting light-emitting mode is preferably such a mode to notify a user that a puff operation is ready to start.

(Control of Magnitude of Power Supply Output in Puff Operation Series)

Figure 8:
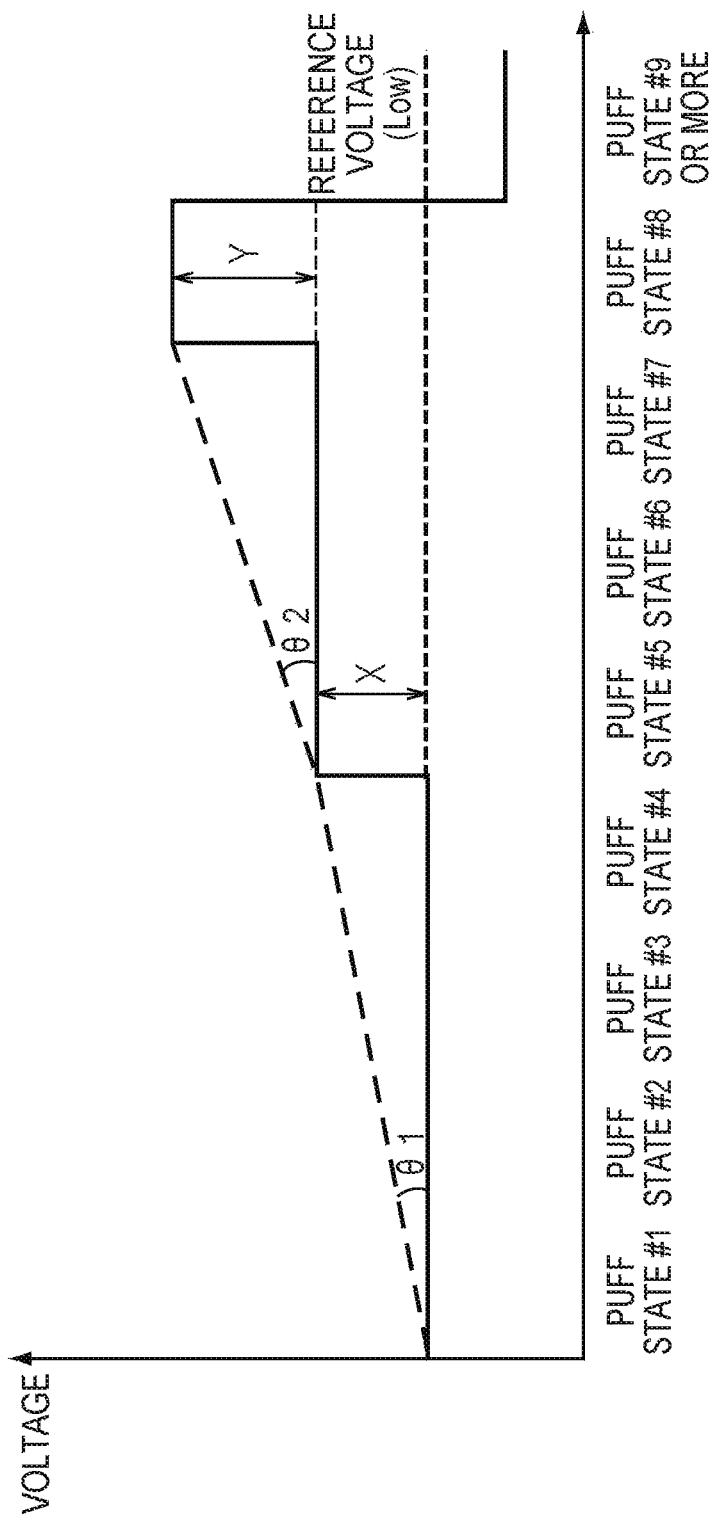
Figure 9:
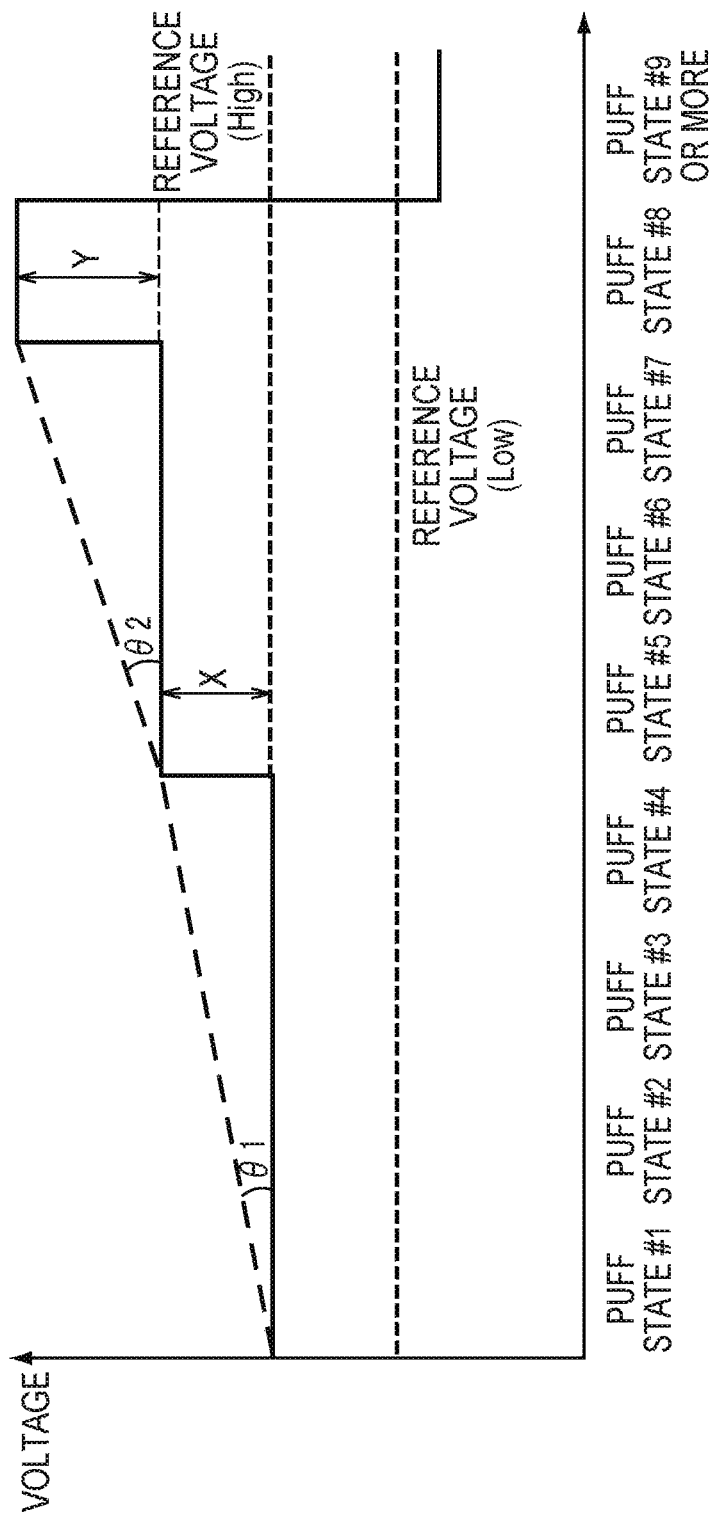

Hereinafter, an example of control of the magnitude of the power supply output in a puff operation series according to the first embodiment will be described. FIGS. 8 and 9 are graphs showing an example of control of the magnitude of the power supply output in a puff operation series according to the first embodiment. FIGS. 8 and 9 exemplify a case where a user should finish a puff operation series in principle when the number of puff operations reaches eight times (predetermined number of times). It should be noted that, since the heat source 80 is not energized in the non-puff state, a behavior of the magnitude of the power supply output in the non-puff state is omitted in FIGS. 8 and 9.

Here, a case is exemplified where the magnitude of the power supply output to the heat source 80 is controlled by a voltage applied to the heat source 80. Therefore, in the first embodiment, control of the magnitude of the power supply output may be considered to be same as control of the voltage. FIG. 8 shows a first mode (Low mode) that uses a first voltage as a reference voltage, and FIG. 9 shows a second mode (High mode) that uses a second voltage higher than the first voltage as the reference voltage. Although the reference voltages are different, the behavior of the voltage applied to the heat source 80 is similar in the first mode (low mode) and the second mode (high mode).

As shown in FIGS. 8 and 9, the heat source control unit 53 increases the voltage applied to the heat source 80 stepwise from the reference voltage along with an increase in the number of puff operations for inhaling aerosol. Specifically, in puff states #1 to #4, the voltage applied to the heat source 80 is constant, and the reference voltage is applied to the heat source 80. In puff states #5 to #7, the voltage applied to the heat source 80 is constant, and a voltage that is one step higher than the reference voltage is applied to the heat source 80. In puff state #8, a voltage that is two steps higher than the reference voltage is applied to the heat source 80. In the 9th and subsequent puff states, a voltage that is smaller than the reference voltage is applied to the heat source 80.

As described above, the heat source control unit 53 increases a gradient of the voltage applied to the heat source 80 along with an increase in the number of puff operations for inhaling aerosol.

For example, along with an increase of the number of puff operations, the number of puff operations, in which a constant voltage is maintained, is decreased. Namely, the number of puff operations applied with the reference voltage is four times, the number of puff operations applied with a voltage one step higher than the reference voltage is three times, and the number of puff operations applied with a voltage two steps higher than the reference voltage is one time. Alternatively, along with an increase of the number of puff operations, the number of puff operations, in which the constant voltage is maintained, is decreased. Alternatively, increase width Y of second time voltage is higher than increase width X of a first step voltage.

Thus, the gradient of the voltage ($\theta1$ and $\theta2$), which is defined by the number of puff operations in which the constant voltage is maintained and by an increase width in which the voltage increases, is increased along with an increase in the number of puff operations. In other words, gradient $\theta2$ in the middle of a puff operation series is larger than gradient $\theta1$ at the beginning of the puff operation series.

Although the voltage applied to the heat source 80 increases in two steps in FIGS. 8 and 9, the embodiment is not limited to this. The voltage applied to the heat source 80 may increase in three or more steps. Alternatively, the voltage applied to the heat source 80 may increase in one step.

(Control of Magnitude of Power Supply Output Per One Puff Operation)

Figure 10:
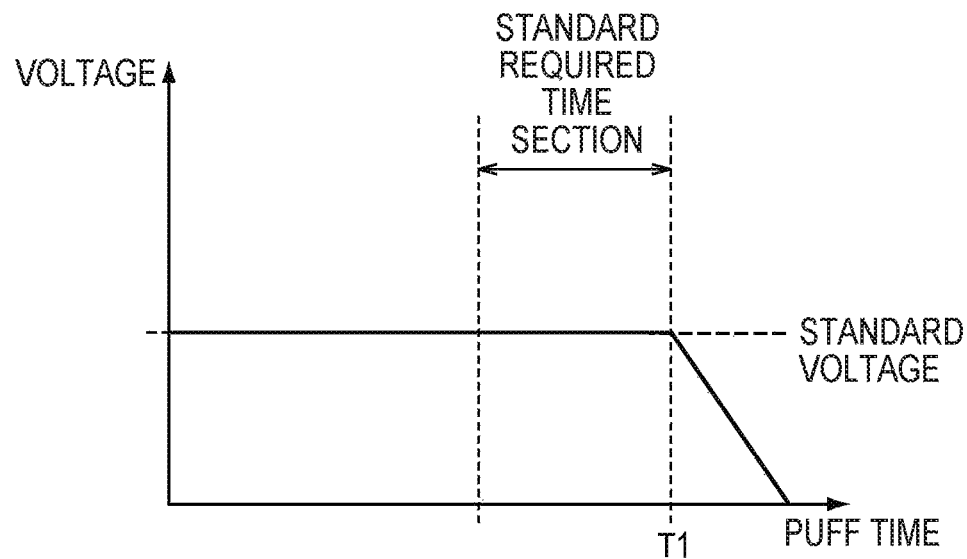
Figure 11:
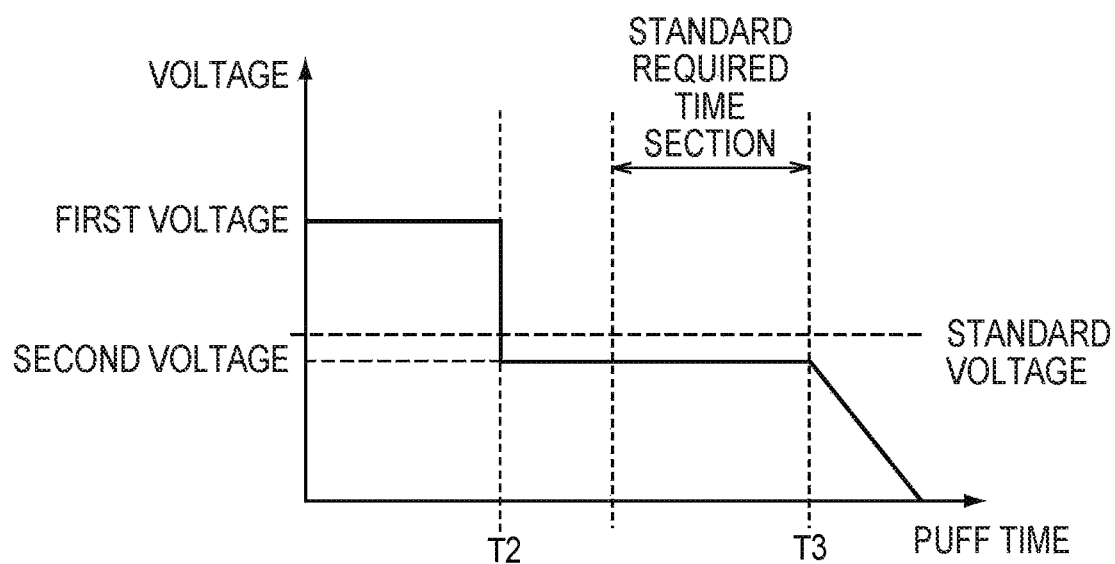

Hereinafter, an example of control of the magnitude of the power supply output per one puff operation according to the first embodiment will be described. FIGS. 10 and 11 are graphs showing an example of control of the magnitude of the power supply output per one puff operation according to the first embodiment. FIGS. 10 and 11 exemplify a case where a user should finish a puff operation series in principle when the number of puff operations reaches eight times (predetermined number of times).

Here, a case is exemplified where the magnitude of the power supply output to the heat source 80 is controlled by a voltage applied to the heat source 80. Therefore, in the first embodiment, control of the magnitude of the power supply output may be considered to be same as control of the voltage. FIG. 10 shows a behavior of the voltage applied to the heat source 80 in the standard mode, and FIG. 11 shows a behavior of the voltage applied to the heat source 80 in the reduced mode.

As shown in FIG. 10, in the standard mode, a standard voltage is applied to the heat source 80 in a duration before a first duration T1 elapses. In the duration after the first duration T1 elapses, a voltage smaller than the standard voltage is applied to the heat source 80.

Here, a case is exemplified where the first duration T1 is same as an end timing of the standard required time duration. However, as described above, the first duration T1 is not limited to this.

As shown in FIG. 11, in the reduced mode, a first voltage higher than the standard voltage is applied to the heat source 80 in a duration before a second duration T2 elapses. In a duration before a third duration T3 elapses after the second duration T2, a second voltage smaller than the first voltage is applied to the heat source 80. In a duration after the third duration T3 elapses, a voltage smaller than the second voltage is applied to the heat source 80.

Here, a case is exemplified where the second duration is shorter than a start timing of the standard required time duration. A case is exemplified where the third duration is same as the end timing of the standard required time duration. A case is exemplified where the second voltage is smaller than the standard voltage. However, the second duration T2, the third duration T3, and the second voltage are not limited to those described above.

In a case where the standard mode or the reduced mode is set, the required time per one puff operation may be changed. It should be noted that, even in such a case, the voltage profile shown in FIG. 10 or FIG. 11 is traced, and the voltage becomes zero immediately after the end of the puff operation. In other words, it should be noted that, since it is sufficient to control the magnitude of the power supply output to the heat source 80 according to a predetermined operation mode, complicated control of continuously controlling the magnitude of the power supply output based on Air flow (inhalation amount) is unnecessary while the heat source 80 is energized.

(Function and Effect)

In the first embodiment, the control circuit 50 (puff detection unit 51) detects the start or end of the puff duration when the slope formed by two or more output values output from the sensor 20 has a predetermined sign (e.g., negative), and the absolute value of slope having the predetermined sign is larger than a predetermined value. This can reduce a possibility of erroneous detection of an output result of the sensor unintended to be a start of the puff duration, such as a pressure change at a high place or vibration of human voice, as the start of the puff duration, and can reduce a possibility that the followability of the magnitude of the power supply output to the heat source 80 is deteriorated, enabling improvement of the detection accuracy of the puff duration. Namely, it is possible to simultaneously improve both the detection accuracy of the puff duration and the followability of the magnitude of the power supply output.

In the first embodiment, in the detection of the start or end of the puff duration, there is used the sensor 20 that outputs the electric capacity of the capacitor, which changes in accordance with the user's puff operation. As shown in FIG. 5, paying attention to a fact that a pressure change in the housing that forms the airflow path is specific at the beginning and end of the inhalation action, a response to detection of the puff duration is improved by using a sensor capable of outputting such a pressure change.

In the first embodiment, the sampling period ($\Delta ta$ or $\Delta tc$) for monitoring the output value output from the sensor 20 outside the puff duration is shorter than the sampling period ($\Delta tb$) for monitoring the output value output from the sensor 20 within the puff duration. This can reduce power required for monitoring the output value output from the sensor 20 in the puff duration while ensuring followability of the magnitude of the power supply output to the heat source 80, by maintaining the detection accuracy of the start of the puff duration. It should be noted that there is no problem even if the detection accuracy of the end of the puff duration is lower than the detection accuracy of the start of the puff duration.

In the first embodiment, before the detection of the start of the puff duration, the control circuit 50 (puff detection unit 51) detects the start of the puff duration when, for consecutive m times of $S(n)$ (m is an integer of 2 or more), a condition that every $S(n)$ is a negative value and the absolute value of every $S(n)$ is larger than the first value is satisfied. On the other hand, after detection of the start of the puff duration, the control circuit 50 (puff detection unit 51) detects the end of the puff duration when, for consecutive m times of $S(n)$, a condition that $S(n)$ is a negative value and the absolute value of $S(n)$ is larger than the first value is satisfied. Thus, in detecting the start or end of the puff duration, it is possible to improve the detection accuracy of the puff duration by using consecutive m times of $S(n)$.

In the first embodiment, in the non-puff state where an aerosol is not inhaled, the light-emitting element control unit 52 controls the light-emitting element 40 in the second light-emitting mode different from the first light-emitting mode. Thus, even in the non-puff state, a user can grasp whether or not the non-combustion type flavor inhaler 100 is in a usable state. Further, since the light-emitting mode in the puff state is different from the light-emitting mode in the non-puff state, it is possible to realize a use feeling similar to a general cigarette that generates an aerosol with burning.

In the first embodiment, the second light-emitting mode changes according to the number of puff operations for inhaling aerosol. Thus, a user can easily grasp a progress status of a puff operation based on the change of the second light-emitting mode in the non-puff state in which it is easy to visually recognize lighting of the light-emitting element 40.

In the first embodiment, the heat source control unit 53 increases the magnitude of the power supply output to the heat source 80 stepwise from the magnitude of the reference power supply output along with an increase in the number of puff operations for inhaling aerosol. Thus, it is possible to bring the supply amount of aerosol close to that of a general cigarette that generates an aerosol with burning, and to realize a use feeling similar to the general cigarette.

In the first embodiment, the tobacco source 131 is arranged on the inhalation side from the holder 60 (aerosol source), and the heat source control unit 53 increases the magnitude of the power supply output to the heat source 80 stepwise from the magnitude of the reference power supply output along with an increase in the number of puff operations for inhaling aerosol. This makes it possible to maintain a supply amount of alkaloid at a level close to a supply amount of alkaloid in an initial puff operation.

Specifically, in a configuration in which alkaloid is contained in the aerosol source as in an existing electronic cigarette, a proportion of alkaloid contained in the aerosol is constant. Therefore, if the magnitude of the power supply output to the heat source 80 is increased stepwise from the magnitude of the reference power supply output by using such a configuration in order to bring the supply amount of aerosol close to that of the general cigarette, the supply amount of alkaloid is increased in proportion to the aerosol supply amount.

On the other hand, in the first embodiment, a configuration is adopted in which the tobacco source 131 is arranged on the inhalation side from the holder 60 (aerosol source). The present inventors have found a phenomenon that the proportion of alkaloid contained in the aerosol is decreased as the number of puff operations increases. Thus, if the magnitude of the power supply output to the heat source 80 is increased stepwise from the magnitude of the reference power supply output in order to bring the supply amount of aerosol close to that of the general cigarette, the supply amount of the alkaloid is maintained at a level close to the supply amount of the alkaloid of the initial puff operation.

As described above, in the first embodiment, in the configuration in which the tobacco source 131 is arranged on the inhalation side from the holder 60 (aerosol source), the heat source control unit 53 increases the magnitude of the power supply output to the heat source 80 stepwise from the magnitude of the reference power supply output along with an increase in the number of puff operations for inhaling aerosol. This makes it possible to maintain a supply amount of alkaloid at a level close to a supply amount of alkaloid in the initial puff operation while bringing the supply amount of aerosol close to that of the general cigarette.

In the first embodiment, the heat source control unit 53 controls a first mode that uses magnitude of a first reference power supply output as the magnitude of the reference power supply output, and a second mode that uses magnitude of a second reference power supply output, which is larger than the magnitude of the first reference power supply output, as the magnitude of the reference power supply output. Thus, a user can select the amount of aerosol depending on user's taste with one non-combustion type flavor inhaler 100.

In the first embodiment, introducing the reduced mode can even increase the satisfaction of such a user whose required time per one puff operation is shorter than the standard required time, by increasing a temperature of the heat source 80 faster than that in the standard mode. Regardless of an operation mode, the magnitude of the power supply output to the heat source is decreased in a duration after the first duration or the third duration elapses, preventing inhalation of decomposed substance and reduction of smoking taste.

In the first embodiment, a predetermined operation mode (standard mode and reduced mode) is prepared, and it is sufficient to control the magnitude of the power supply output to the heat source according to the predetermined operation mode. Consequently, complicated control of continuously controlling the magnitude of the power supply output based on Air flow (inhalation amount) is unnecessary while the heat source 80 is energized. In other words, it is possible to realize reduction of smoking taste, and improvement of the user's satisfaction with a simple configuration.

[Modified Example 1]

Hereinafter, Modified Example 1 of the first embodiment will be described. In the following, differences from the first embodiment will be mainly described.

Specifically, in the above-described first embodiment, the heat source control unit 53 controls the magnitude of the power supply output to the heat source 80 from the power source 10 by controlling the voltage applied to the heat source 80 from the power source 10. In detail, by increasing the voltage applied to the heat source 80 stepwise from the reference voltage along with an increase in the number of puff operations for inhaling aerosol, the heat source control unit 53 increases the magnitude of the power supply output to the heat source 80 stepwise from the magnitude of the reference power supply output (see FIGS. 8 and 9).

Figure 12:
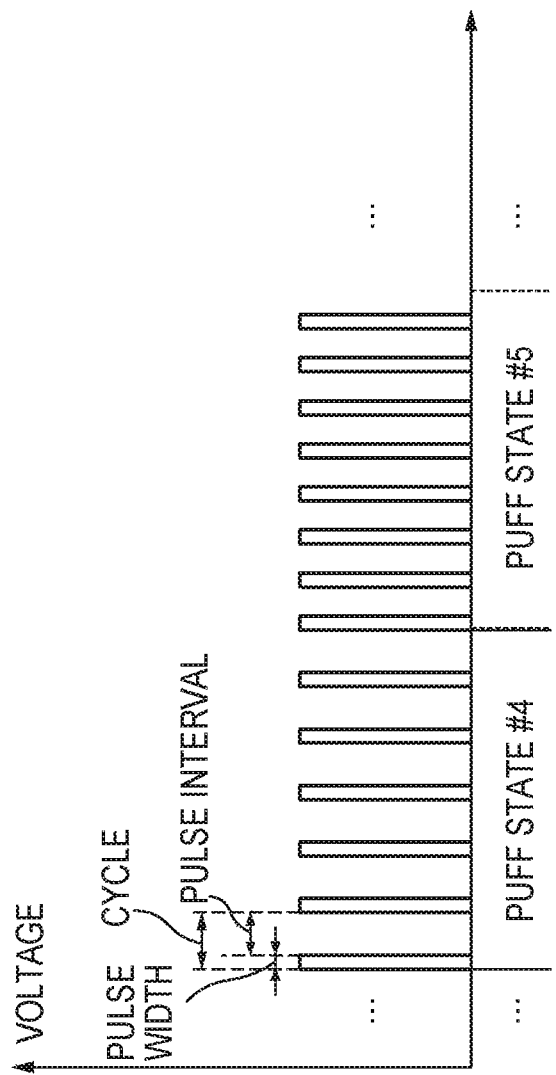

On the other hand, in Modified Example 1, the heat source control unit 53 controls the voltage applied from the power source 10 to the heat source 80 by duty control, and controls the magnitude of the power supply output to the heat source 80 from the power source 10 by controlling the duty ratio of the voltage applied to the heat source 80. As shown in FIG. 12, 1 cycle is defined by a pulse width and a pulse interval, and the duty ratio is represented by a pulse width/1 cycle (here, 1 cycle=pulse width+pulse interval). Specifically, the heat source control unit 53 increases the duty ratio of the voltage applied to the heat source 80 along with an increase in the number of puff operations for inhaling aerosol (see FIG. 12).

FIG. 12 exemplifies a case where the magnitude of the power supply output is increased between puff states #4 and #5, following the examples shown in FIGS. 8 and 9. Although the puff states other than puff states #4 and #5 are omitted in FIG. 12, it is needless to say that the effect similar to that of the case shown in FIGS. 8 and 9 can be obtained by controlling the duty ratio.

[Modified Example 2]

Hereinafter, Modified example 2 of the first embodiment will be described. In the following, differences from the first embodiment will be mainly described.

Specifically, in the above-described first embodiment, the heat source control unit 53 controls the magnitude of the power supply output to the heat source 80 from the power source 10 by controlling the voltage applied to the heat source 80 from the power source 10. In detail, by increasing the voltage applied to the heat source 80 stepwise from the reference voltage along with an increase in the number of puff operations for inhaling aerosol, the heat source control unit 53 increases the magnitude of the power supply output to the heat source 80 stepwise from the magnitude of the reference power supply output (see FIGS. 8 and 9).

Figure 13:
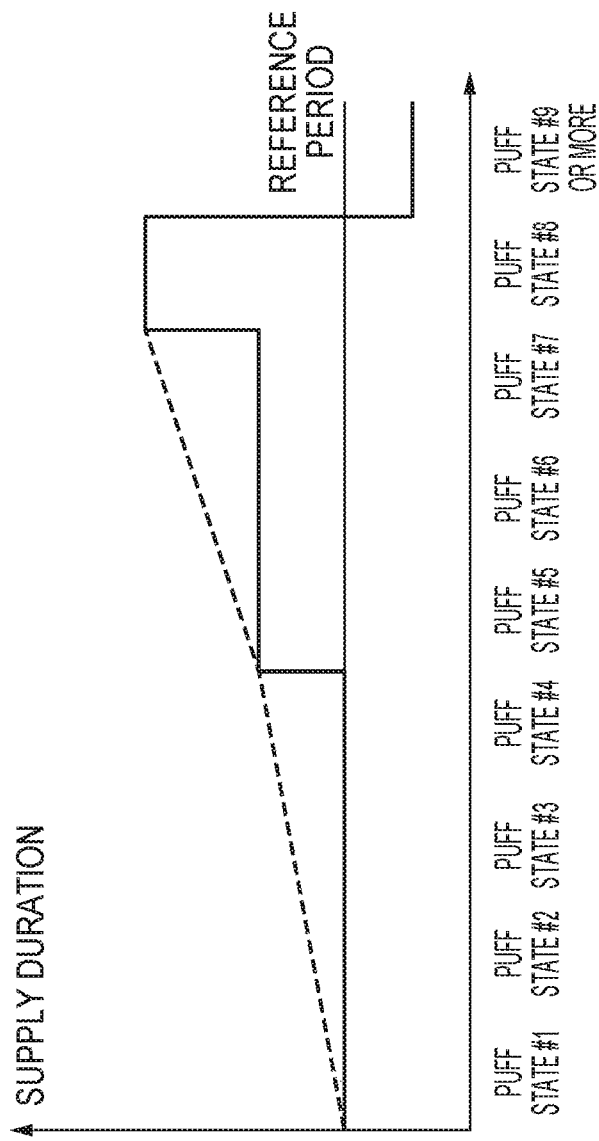

On the other hand, in Modified Example 2, the heat source control unit 53 controls the power supply output (power supply amount) to the heat source 80 by controlling the maximum period (supply duration) in which the heat source 80 is continuously energized. Specifically, the heat source control unit 53 stepwise extends the maximum period (supply duration) for continuing energization to the heat source 80 from a reference period, along with an increase in the number of puff operations for inhaling aerosol (see FIG. 13).

In Modified Example 2, when the supply duration has elapsed since the energization to the heat source 80 has been started, the energization to the heat source 80 is stopped. The first light-emitting mode of the light-emitting element 40 is maintained while the user continues the puff operation even if the energization is stopped. This changes the power supply output (power supply amount) to the heat source 80 per one puff operation, providing similar effect as the example shown in FIGS. 8 and 9.

When the standard mode and the reduced mode described in the first embodiment are introduced, the first duration, the second duration, and the third duration may be adjusted (extended) along with an increase in the number of puff operations for inhaling aerosol.

[Modified Example 3]

Hereinafter Modified example 3 of the first embodiment will be described. In the following, differences from the first embodiment will be mainly described.

Specifically, in the first embodiment above, as described in detail in the first embodiment, before the detection of the start of the puff duration, the control circuit 50 (puff detection unit 51) detects the start of the puff duration when, for consecutive m times (m is an integer of 2 or more) of S(n), a condition that every S(n) is a negative value and the absolute value of every S(n) is larger than the first value is satisfied. As a result, even in a case where a user blows in from the inhalation portion of the non-combustion type flavor inhaler 100 toward inside of the non-combustion type flavor inhaler 100, a possibility of erroneous detection of such an operation as the start of the puff duration can be reduced.

On the other hand, in Modified Example 3, there is further provided a means that detects blowing when a user blows in, and notifies the user that the blowing has been detected.

Specifically, before the detection of the start of the puff duration, the control circuit 50 (puff detection unit 51) detects the start of the blowing when, for the consecutive m times of S(n), a condition that every S(n) is a positive value and the absolute value of every S(n) is larger than the first value is satisfied. Namely, in Modified Example 3, blowing is detected by using a fact that a sensor output pattern obtained in performing of the blowing has an opposite sign of positive or negative with respect to a pattern obtained in performing of the puff operation.

When blowing is detected in the puff detection unit 51, the light-emitting element control unit 52 controls the light-emitting element 40 in a light-emitting mode different from the first light-emitting mode and the second light-emitting mode described above. Namely, in Modified Example 3, by controlling the light-emitting element 40 in the light-emitting mode different from the above-described first light-emitting mode and second light-emitting mode, detection of the blowing is notified to a user.

Needless to say, when blowing is detected in the puff detection unit 51, as in the first embodiment, the heat source control unit 53 does not energize the heat source 80 from the power source 10.

[Modified Example 4]

Hereinafter, Modified example 4 of the first embodiment will be described. In the following, differences from the first embodiment are mainly described below.

In Modified Example 4, based on the slope absolute value, the control circuit 50 (heat source control unit 53) controls the power supply output to the heat source 80 (atomizing part) such that the aerosol amount, which is an amount of the aerosol atomized by the heat source 80 (atomizing part), falls within a desired range in one energization to the heat source 80 (atomizing part). It should be noted that one energization to the heat source 80 (atomizing part) is energization corresponding to one puff operation. A timing of determining a control method of the power supply output is preferably similar to a timing of detecting the start of the puff duration described in the first embodiment. It should be noted that, in the first embodiment, there is used the sensor 20 that outputs the value indicating the electric capacity of the capacitor. However, the timing of determining the control method of the power supply output is not limited to this, and it may be a timing of detecting the start of the puff duration by another method.

Here, in the first embodiment, the output value output from the sensor 20 is a value (e.g., a voltage value or a current value) indicating the electric capacity of the capacitor. A response value derived from the output value is the output value itself output from the sensor 20. That is, the response value is a value (e.g., a voltage value) indicating the electric capacity of the capacitor.

On the other hand, in Modified Example 4, the output value output from the sensor 20 is not limited to the value indicating the electric capacity of the capacitor, but may be a value that changes in accordance with the air inhaled from the inhalation side toward the inhalation side (i.e. user's puff operation). In other words, the output value output from the sensor 20 may be a value (e.g., a voltage value or a current value) indicating an environment (e.g., a pressure or a flow rate in the housing) that changes in accordance with the user's puff operation. The output value output from the sensor 20 may be a value itself indicating an environment that changes in accordance with the user's puff operation, or may be a value obtained by predetermined conversion of the value. For example, the output value may be a flow rate value obtained by conversion of a value detected by the sensor 20 (value indicating a pressure). Similarly, the response value derived from the output value may be the output value itself output from the sensor 20, or may be a value (e.g., a flow rate value) obtained by predetermined conversion of the output value output from the sensor 20.

For example, when the output value is the flow rate value obtained by conversion of the value indicating a pressure, the sensor 20 obtains the flow rate value based on an amplitude or frequency of a waveform obtained by plotting the value detected by the sensor 20 (value indicating a pressure) on a time axis. As a result, the sensor 20 can output the flow rate value by predetermined conversion of the value detected by the sensor 20. In a case where the condenser microphone sensor described in the first embodiment is used as the sensor 20, when the response value is a flow rate value obtained by conversion of the value indicating a pressure, the control circuit 50 obtains the flow rate value based on an amplitude or frequency of a waveform obtained by plotting the output value output from the sensor 20 (value indicating a pressure) on the time axis. As a result, a response value (e.g., a flow rate value) can be obtained by predetermined conversion of the output value output from the sensor 20.

Firstly, the control circuit 50 controls the magnitude of the power supply output to the heat source 80 (atomizing part) such that the aerosol amount falls within a desired range.

In a case where a voltage is continuously applied to the heat source 80 (atomizing part), the magnitude of the power supply output is controlled by a value of the voltage applied to the heat source 80 (atomizing part). On the other hand, in a case where a voltage is intermittently applied to the heat source 80 (atomizing part) (duty control), the magnitude of the power supply output is controlled by a value of the voltage applied to the heat source 80 (atomizing part) and the duty ratio.

In other words, as described above, the magnitude of the power supply output to the heat source 80 can be expressed by, for example, $P=\{(D_2 \times V)^2/R\} \times D_1$.

Specifically, the control circuit 50 preferably increases the magnitude of the power supply output to the heat source 80 (atomizing part) as the slope absolute value is larger. This can prevent a decrease of a total amount of aerosol to be inhaled by a user who performs a short and deep puff operation, as compared with a user who performs a long and shallow puff operation, under a premise that an inhalation action is performed with a same inhalation capacity. The shallow puff operation is a puff operation with a relatively small slope absolute value, and the deep puff operation is a puff operation with a relatively large slope absolute value.

Alternatively, the control circuit 50 may use a predetermined magnitude as the magnitude of the power supply output to the heat source 80 (atomizing part) when the slope absolute value is within a predetermined range. In such a case, the control circuit 50 increases the magnitude of the power supply output to the heat source 80 (atomizing part) to be larger than the predetermined magnitude when the slope absolute value is larger than the predetermined range. This can prevent a decrease of a total amount of aerosol to be inhaled by a user who performs a short and deep puff operation, as compared with a user who performs a standard puff operation. On the other hand, the control circuit 50 may decrease the magnitude of the power supply output to the heat source 80 (atomizing part) to be smaller than the predetermined magnitude when the slope absolute value is smaller than the predetermined range. This can prevent an increase of a total amount of aerosol to be inhaled by a user who performs a long and shallow puff operation, as compared with a user who performs a standard puff operation.

Secondly, when the supply duration has elapsed since the energization to the heat source 80 (atomizing part) has been started, the control circuit 50 stops the energization to the heat source 80 (atomizing part) such that the aerosol amount falls within a desired range. The supply duration is preferably equal to or less than an upper limit value of the standard puff duration derived from statistics of the puff duration of the user.

For example, the supply duration is 1 second or more to 3 seconds or less. Since the supply duration is 1 second or more, an energizing time of the heat source 80 (atomizing part) is not too short as compared with the puff duration, reducing a sense of discomfort given to the user. On the other hand, since the supply duration is 3 seconds or less, it is possible to set the number of puff operations, in which the energizing time of the heat source 80 (atomizing part) is fixed to the supply duration, to a certain number or more.

Further, the supply duration may also be 1.5 seconds or more to 2.5 seconds or less. This further reduces the sense of discomfort given to the user, and allows increase in the puff operation in which the energizing time of the heat source 80 (atomizing part) is fixed to the supply duration.

Note that the standard puff duration can be derived from the statistics of a puff duration of a user, and the standard puff duration is a duration between a lower limit value in the puff durations of the plurality of users and an upper limit value in the puff durations of the plurality of users. The lower limit value and the upper limit value may be, for example, derived as a lower limit value and an upper limit value of a 95% confidence interval of an average value based on a distribution of puff duration data of a user, and may be derived as m±nσ (here, m is an average value, σ is a standard deviation, and n is a positive real number). For example, in a case where the user's puff duration can be regarded as following a normal distribution in which the average value m is 2.4 seconds and the standard deviation σ is 1 second, the upper limit value of the standard puff duration can be derived as m+nσ as described above, which is about 3 to 4 seconds.

In detail, in addition to the control of the magnitude of the power supply output described above, the control circuit 50 preferably reduces the supply duration as the slope absolute value is larger. This can prevent an excessive increase of the total amount of aerosol to be inhaled by a user who performs a deep puff operation (in particular, a long and deep puff operation).

Alternatively, in addition to the control of the magnitude of the power supply output described above, the control circuit 50 may use a predetermined duration as the supply duration when the slope absolute value is within the predetermined range. In such a case, the control circuit 50 preferably reduces the supply duration to be shorter than the predetermined duration when the slope absolute value is larger than the predetermined range. This can prevent an excessive increase of the total amount of aerosol to be inhaled by a user who performs a deep puff operation (in particular, a long and deep puff operation) as compared with a user who performs a standard puff operation. On the other hand, when the slope absolute value is smaller than the predetermined range, the control circuit 50 preferably uses the predetermined duration as the supply duration without reducing the supply duration.

Figure 14:
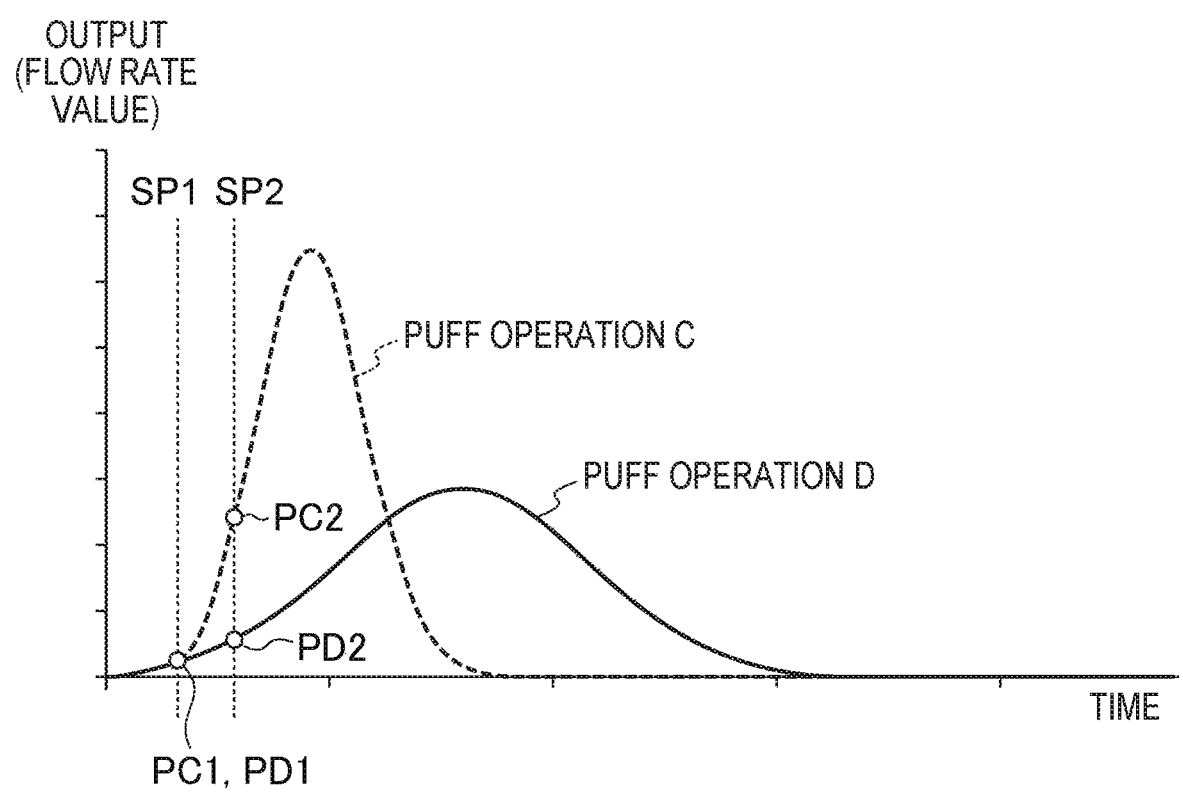

For example, as shown in FIG. 14, description will be given by exemplifying puff operation C and puff operation D with different changing modes of response values (here, flow rate values). Puff operation C is a shorter and deeper puff operation than puff operation D. Here, puff operation C is an example of a shorter and deeper puff operation than the standard puff operation, and puff operation D is an example of a longer and shallower puff operation than the standard puff operation. In other words, the slope absolute value corresponding to puff operation C is larger than the predetermined range, and the slope absolute value corresponding to puff operation D is smaller than the predetermined range.

Here, a capacity of air (inhalation capacity) to be inhaled by puff operation C is same as a capacity of air (inhalation capacity) to be inhaled by puff operation D. However, it should be noted that, when it is assumed that the magnitude of the power supply output to the heat source 80 (atomizing part) is constant between the puff operation C and puff operation D, since the puff duration of puff operation C is shorter than the puff duration of puff operation D, a total amount of aerosol to be inhaled by puff operation C is less than a total amount of aerosol to be inhaled by puff operation D.

In such a case, the control circuit 50 controls the magnitude of the power supply output to the heat source 80 (atomizing part) such that the magnitude of the power supply output to the heat source 80 (atomizing part) in puff operation C is larger than the magnitude of the power supply output to the heat source 80 (atomizing part) in puff operation D. Further, in addition to the control of the magnitude of the power supply output, the control circuit 50 may control the supply duration such that the supply duration used in puff operation C is shorter than the supply duration used in puff operation D.

Alternatively, as for puff operation C, since the slope absolute value is larger than the predetermined range at timing SP2, the control circuit 50 increases the magnitude of the power supply output to the heat source 80 (atomizing part) to be larger than the predetermined magnitude. Furthermore, in addition to the control of the magnitude of the power supply output, the control circuit 50 preferably reduces the supply duration to be shorter than the predetermined duration. On the other hand, as for puff operation D, the slope absolute value is smaller than the predetermined range at timing SP2, the control circuit 50 uses the predetermined duration as the supply duration without reducing the supply duration. For puff operation D, the control circuit 50 may reduce the magnitude of the power supply output to the heat source 80 (atomizing part) to be smaller than the predetermined magnitude.

It should be noted that, in Modified Example 4, the control circuit 50 stops the energization to the heat source 80 (atomizing part) even if the puff operation is continued, when the supply duration has elapsed since the energization to the heat source 80 (atomizing part) has been started. In such a case, even after the energization to the heat source 80 is stopped, the control circuit 50 preferably continues to control the light-emitting element 40 in the first light-emitting mode, if the puff operation for inhaling aerosol is continued. This reduces the sense of discomfort that the light-emitting pattern of the light-emitting element 40 is changed despite the puff operation being performed.

In Modified Example 4, attention is paid to one puff operation. However, as shown in FIGS. 8 and 9, Modified Example 4 can be applied to a case where the magnitude of the power supply output to the heat source 80 is increased stepwise from the magnitude of the reference power supply output along with an increase in the number of puff operations. In such a case, it may be considered that the desired range is set to be increased stepwise in accordance with the number of puff operations. For example, in the cases shown in FIGS. 8 and 9, a desired range in puff state #5 may be larger than a desired range in puff state #1.

(Function and Effect)

In Modified Example 4, the control circuit 50 controls the magnitude of the power supply output to the heat source 80 (atomizing part) such that the aerosol amount falls within a desired range based on the slope absolute value. Namely, by estimating a mode of puff operation for each puff operation based on the slope absolute value, it is possible to appropriately and quickly control the total amount of the aerosol to be inhaled by a user for each puff operation.

In Modified Example 4, the control circuit 50 increases the magnitude of the power supply output to the heat source 80 (atomizing part) as the slope absolute value is larger. This can prevent a decrease of a total amount of aerosol to be inhaled by a user who performs a short and deep puff operation, as compared with a user who performs a long and shallow puff operation.

In Modified Example 4, the control circuit 50 increases the heat source 80 (the magnitude of the power supply output to atomizing part) to be larger than the predetermined magnitude when the slope absolute value is larger than the predetermined range. This can prevent a decrease of a total amount of aerosol to be inhaled by a user who performs a short and deep puff operation, as compared with a user who performs a standard puff operation.

In Modified Example 4, as the slope absolute value is larger, the supply duration is reduced. This can prevent an excessive increase of the total amount of aerosol to be inhaled by a user who performs a deep puff operation (in particular, a long and deep puff operation).

In Modified Example 4, the control circuit 50 reduces the supply duration to be shorter than the predetermined duration when the slope absolute value is larger than the predetermined range. This can prevent an excessive increase of the total amount of aerosol to be inhaled by a user who performs a deep puff operation (in particular, a long and deep puff operation) as compared with a user who performs a standard puff operation.

[Modified Example 5]

Hereinafter, Modified Example 5 of the first embodiment will be described. In the following, differences from Modified Example 4 will be mainly described.

In Modified Example 5, a relationship between the magnitude of the power supply output to the heat source 80 (atomizing part) and a supply duration will be described. Here, in order to clarify the description, a puff operation is classified into a first puff operation (Normal) and a second puff operation (Boost) in accordance with the slope absolute value, and a relative relationship of these is exemplified. The magnitude of the power supply output to the heat source 80 can be expressed by $P=\{(D_2 \times V)^2/R\} \times D_1$. The first puff operation is a puff operation having a first slope absolute value, and the second puff operation is a puff operation having a second slope absolute value larger than the first slope absolute value.

In such a case, for the second puff operation, the control circuit 50 increases the magnitude of the power supply output to the heat source 80 and reduces the supply duration, as compared with the first puff operation. For example, the magnitude of the power supply output of the first puff operation is represented by $PX_1$, the supply duration of the first puff operation is represented by $TX_1$, the magnitude of the power supply output of the second puff operation is represented by $PX_2$, and the supply duration of the second puff operation is represented by $TX_2$.

Figure 15:
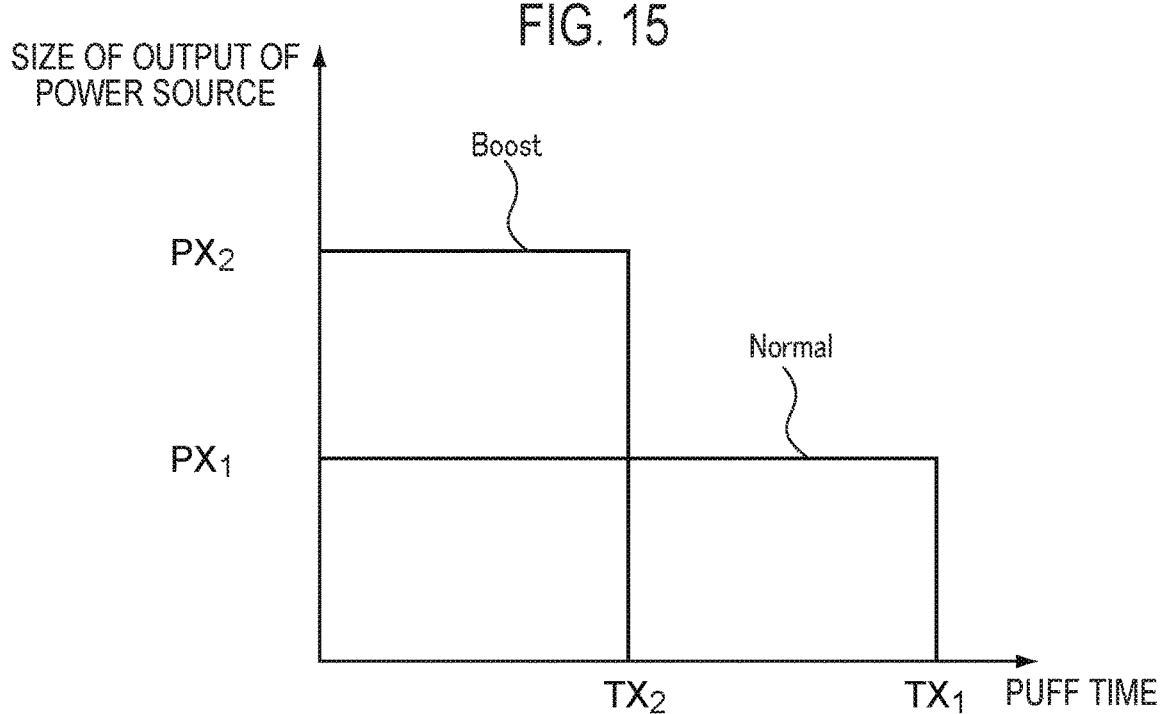
Figure 16:
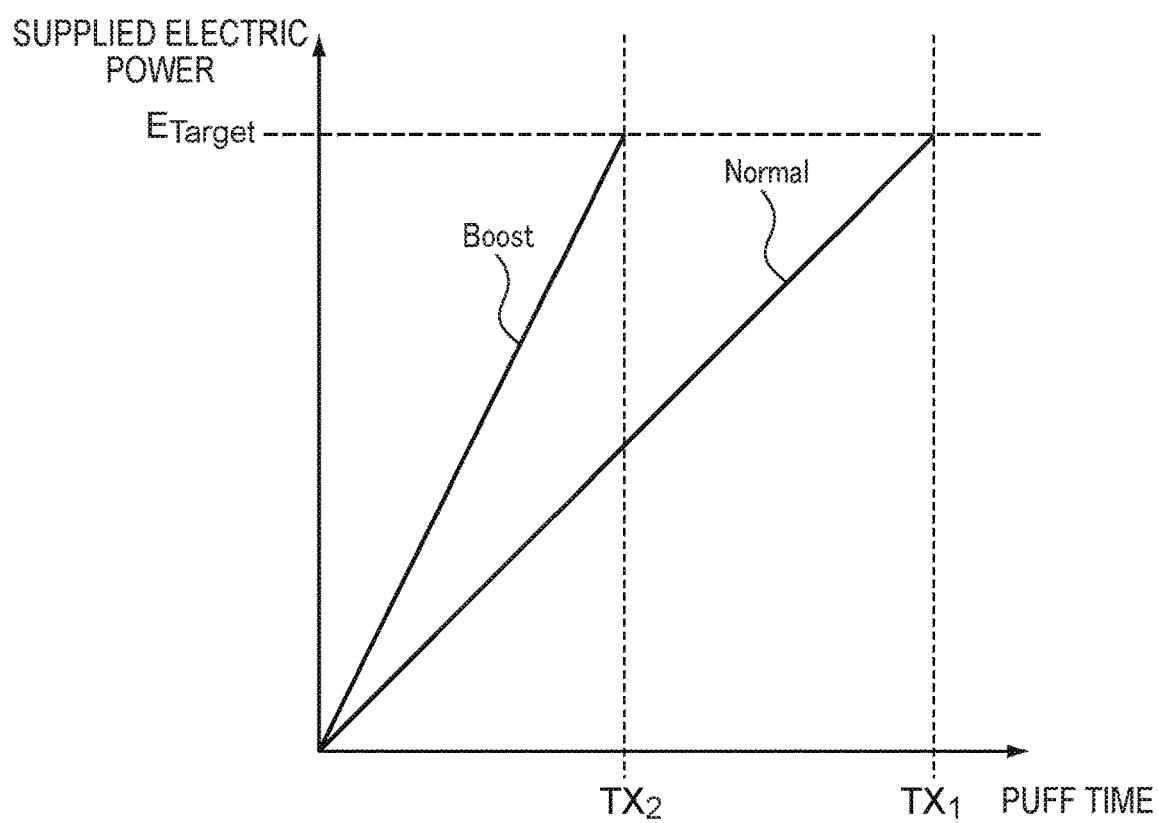

FIG. 15 is a graph showing a relationship between the magnitude of the power supply output and a time for the first puff operation and the second puff operation, and FIG. 16 is a graph showing a relationship between a power supply amount and a time for the first puff operation and the second puff operation. As shown in FIGS. 15 and 16, $PX_1$ and $TX_1$ of the first puff operation are set such that the power supply amount (here, $E_1 = PX_1 \times TX_1$) satisfies a target power amount ($E_{Target}$). Similarly, $PX_2$ and $TX_2$ of the second puff operation are set such that the power supply amount (here, $E_2 = PX_2 \times TX_2$) satisfies the target power amount ($E_{Target}$). In other words, a relationship of $PX_1 \times TX_1 = PX_2 \times TX_2 = E_{Target}$ is satisfied for the first puff operation and the second puff operation. However, $PX_1$ and $TX_1$ of the first puff operation are reference values, which are previously stored by the control circuit 50. Accordingly, when $PX_2$ of the second puff operation is determined, $TX_2$ of the second puff operation is determined according to the expression $TX_2 = (PX_1/PX_2) \times TX_1$.

Here, $PX_2$ of the second puff operation is determined according to the second slope absolute value. $PX_2$ of the second puff operation may be determined based on a function in which the magnitude of the power supply output is increased as the second slope absolute value is larger. Alternatively, $PX_2$ of the second puff operation may be associated with the second slope absolute value. For example, under a premise that the magnitude of the power supply output is $PX_1$ when the slope absolute value is less than threshold value A, the magnitude of the power supply output may be $PX_{2-1}$ when the slope absolute value is equal to or larger than threshold value A and less than threshold value B, and magnitude of the power supply output may be $PX_{2-2}$ larger than $PX_{2-1}$ when the slope absolute value is equal to or larger than threshold value B. Here, although the magnitude of the power supply output of two steps ($PX_{2-1}$ and $PX_{2-2}$) is exemplified, $PX_2$ of the second puff operation may be classified into three or more steps according to the slope absolute value.

Here, a value that can be taken by an increase rate ($PX_2/PX_1$) of the magnitude of the power supply output of the second puff operation with respect to the first puff operation is preferably larger than 1 to 3 or less. Further, the value that can be taken by the increase rate ($PX_2/PX_1$) is preferably larger than 1 to 2 or less. On the other hand, a value that can be taken by the reduction rate ($TX_2/TX_1$) of the supply duration of the second puff operation with respect to the first puff operation is preferably ⅓ or more to less than 1. Further, the value that can be taken by the reduction rate ($TX_2/TX_1$) is preferably ½ or more to less than 1.

Even when $PX_2$ can change to n kinds or more (n is an integer of 3 or more) according to the second slope absolute value, the value that can be taken by $PX_2$ ($\{PX_{2-1}, PX_{2-2}, \ldots PX_{2-n}\}$) is preferably larger than 1 to 3 or less. On the other hand, even when $TX_2$ can change to n kinds or more (n is an integer of 3 or more) according to the second slope absolute value, the value that can be taken by $TX_2$ ($\{TX_{2-1}, TX_{2-2}, \ldots TX_{2-n}\}$) is preferably ⅓ or more to less than 1.

In FIGS. 15 and 16, the magnitude of the power supply output to the heat source 80 is represented by $\{(D_2 \times V)^2/R\} \times D_1$. The magnitude of the power supply output may be controlled by $D_1$, or may be controlled by $D_2$.

In Modified Example 5, attention is paid to one puff operation. However, as shown in FIGS. 8 and 9, Modified Example 5 can be applied to a case where the magnitude of the power supply output to the heat source 80 is increased stepwise from the magnitude of the reference power supply output along with an increase in the number of puff operations. In such a case, it may be considered that the target power amount ($E_{Target}$) is set to be increased stepwise in accordance with the number of puff operations. For example, in the cases shown in FIGS. 8 and 9, the target power amount ($E_{Target}$) in puff state #5 may be larger than the target power amount ($E_{Target}$) in puff state #1.

[Modified Example 6]

Hereinafter, Modified Example 6 of the first embodiment will be described. In the following, differences from Modified Example 5 will be mainly described.

Specifically, in Modified Example 5, the case has been exemplified where the magnitude $PX_2$ of the power supply output of the second puff operation is constant through one energization (puff operation). On the other hand, in Modified Example 6, a case will be exemplified where the magnitude $PX_2$ of the power supply output of the second puff operation is variable within one energization (puff operation).

In Modified Example 6, the control circuit 50 reduces the magnitude $PX_2$ of the power supply output to the heat source 80 as the elapsed time (i.e. elapsed puff time) from the start of energization to the heat source 80 (atomizing part) in one energization (puff operation) becomes longer.

Figure 17:
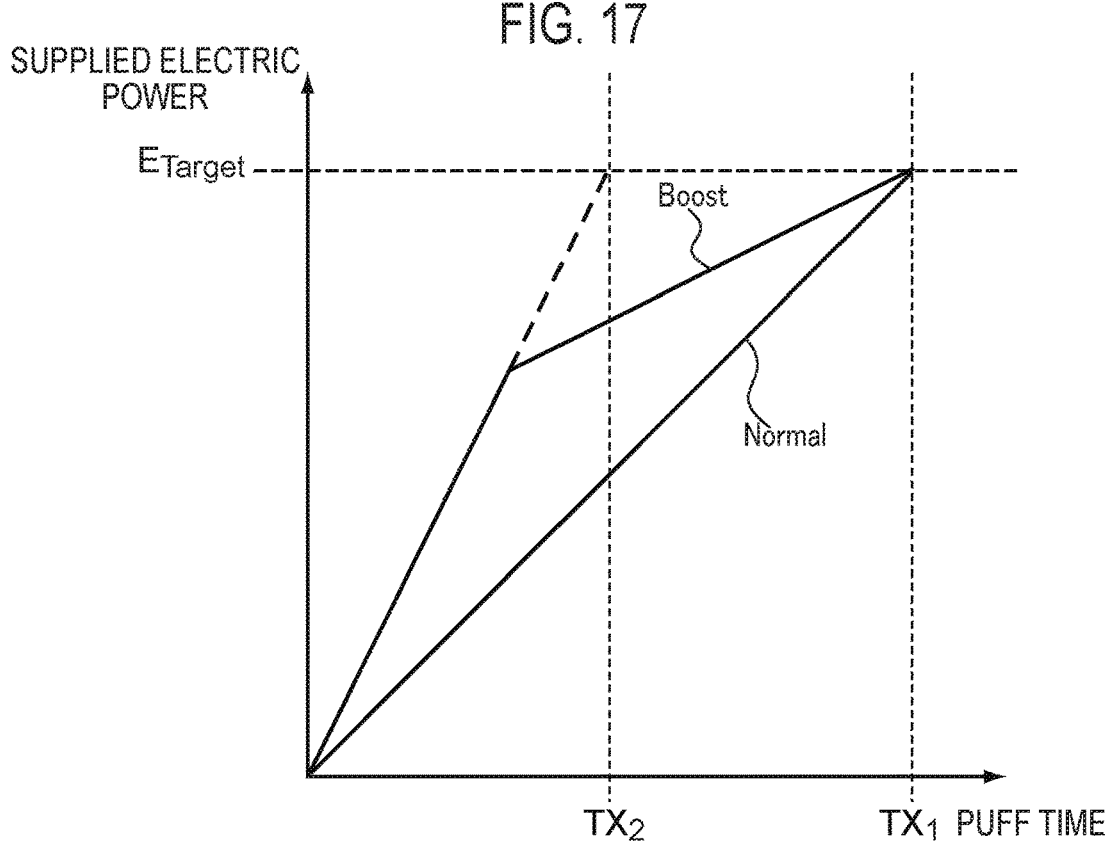

For example, as shown in FIG. 17, the magnitude $PX_2$ of the power supply output to the heat source 80 may be decreased stepwise (discontinuously) according to the elapsed puff time. In the case shown in FIG. 17, a case is exemplified where the magnitude $PX_2$ of the power supply output is changed in two steps, but Modified Example 6 is not limited to this case, but the magnitude $PX_2$ of the power supply output may be set to three or more steps. The magnitude $PX_2$ of the power supply output is determined such that the power supply amount reaches the target power amount ($E_{Target}$) when the supply duration (here, $TX_1$) elapses.

Figure 18:
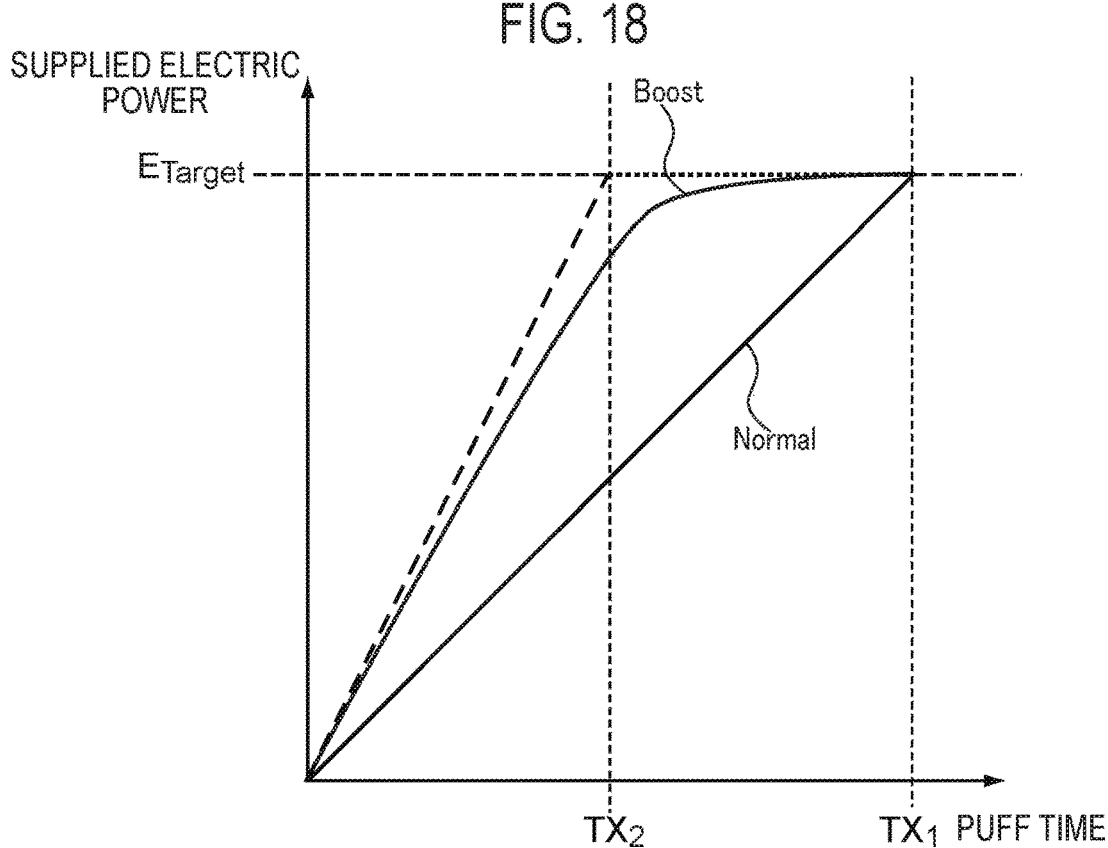

Alternatively, as shown in FIG. 18, the magnitude $PX_2$ of the power supply output to the heat source 80 may be continuously decreased in accordance with the elapsed puff time. The magnitude $PX_2$ of the power supply output is determined such that the power supply amount reaches the target power amount ($E_{Target}$) when the supply duration (here, $TX_1$) elapses.

Thus, the magnitude $PX_2$ of the power supply output to the heat source 80 is decreased as the elapsed puff time becomes longer such that the power supply amount reaches the target power amount ($E_{Target}$) with the elapse of $TX_1$ longer than $TX_2$, providing the following effects as compared with Modified Example 5 (FIGS. 15 and 16). Here, a case is considered where the puff time of a user is longer than $TX_2$ in a case where the user performs the second puff operation (Boost) in which the slope absolute value is the second slope absolute value.

In such a case, in Modified Example 5, when the puff time exceeds $TX_2$, the energization to the heat source 80 is stopped. On the other hand, in Modified Example 6, since the energization to the heat source 80 continues until the puff time reaches $TX_1$ longer than $TX_2$, even if a user who performs a deep puff operation accidentally performs a puff operation longer than $TX_2$, an energizing time of the heat source 80 (atomizing part) is not too short as compared with the puff duration, reducing a sense of discomfort given to the user.

In Modified Example 6, although the magnitude $PX_2$ of the power supply output of the second puff operation (Boost) has been described as an example, Modified Example 6 is not limited to this. The control circuit 50 may decrease the magnitude $PX_1$ of the power supply output to the heat source 80 in the first puff operation (Normal) as the elapsed puff time increases. Needless to say, even in this case, the magnitude $PX_1$ of the power supply output is controlled such that the power supply amount reaches the target power amount ($E_{Target}$) at a time when the supply duration has been reached.

[Modified Example 7]

Hereinafter, Modified Example 7 of the first embodiment will be described. In the following, differences from Modified Example 5 will be mainly described.

Specifically, in Modified Example 7, the control circuit 50 determines the magnitude of the power supply output to the heat source 80 (atomizing part) based on the slope absolute value, and also determines the supply duration based on a learning result of required time for a user's puff operation.

For example, the control circuit 50 stores a plurality of required-time samples by learning the required time for the user's puff operation, derives a representative value of the plurality of the stored required-time samples, and determines the supply duration based on the representative value. As the representative value, an average value, a median, or a mode of the plurality of required-time samples can be used.

For example, the second puff operation (Boost) described in Modified Example 5 will be described as an example. The second puff operation is a puff operation having a second slope absolute value larger than the first slope absolute value, as described above. Additionally, a case is assumed where the representative value of the required-time samples obtained by learning is longer than $TX_2$ described above and shorter than $TX_1$ described above.

Figure 19:
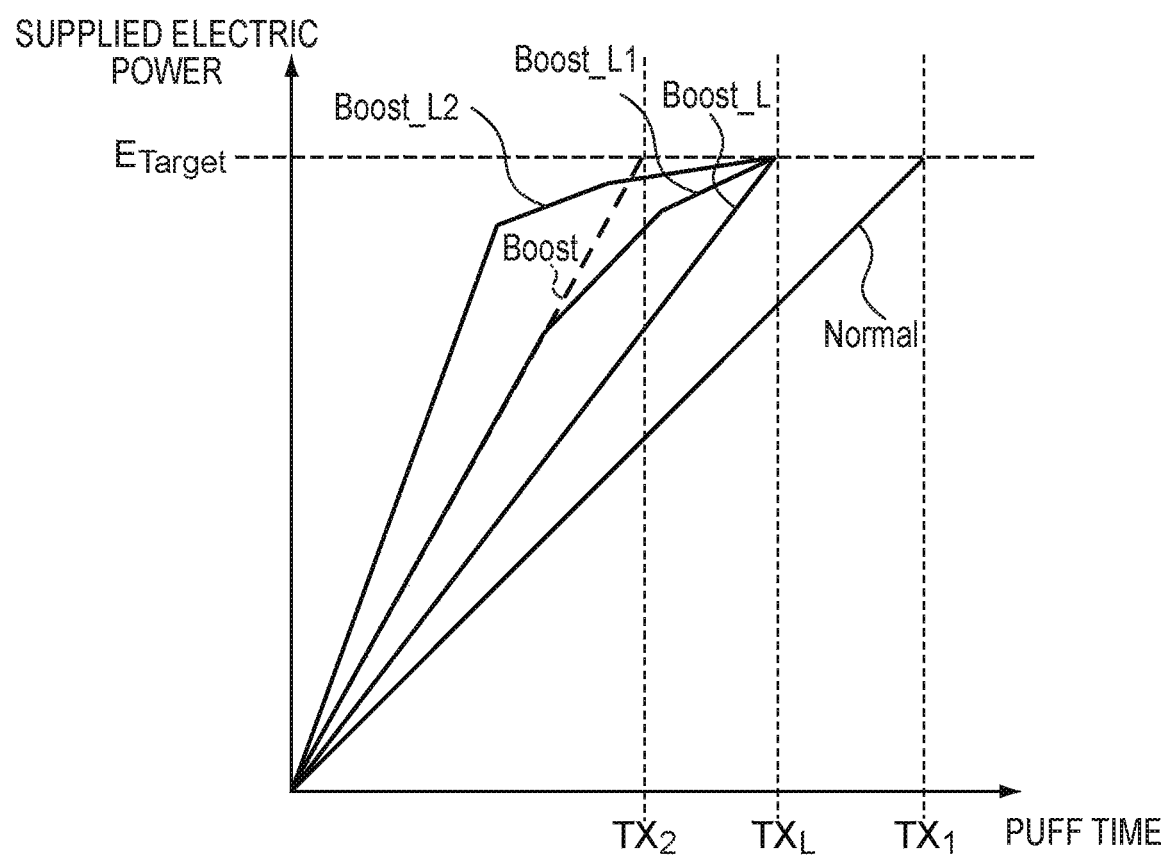

In such a case, as shown in FIG. 19, the supply duration is corrected to $TX_L$ ($TX_2 < TX_L < TX_1$), and the magnitude $PX_L$ of the power supply output is corrected such that the power supply amount reaches the target power amount ($E_{Target}$) when $TX_L$ has elapsed.

For example, the magnitude of the power supply output may be corrected from $PX_2$ to $PX_L$ ($PX_1 < PX_L < PX_2$) (see puff operation (Boost_L) in FIG. 19).

Alternatively, the control circuit 50 may determine the magnitude of the power supply output based on the slope absolute value. Specifically, the control circuit 50 may determine the magnitude of the power supply output such that the power supply amount increases at a stage earlier than the puff operation (Boost_L) as the slope absolute value is larger (see puff operation (Boost_L1 and Boost_L2) in FIG. 19). In such a case, like Modified Example 6, the magnitude of the power supply output may be determined such that the power supply amount reaches the target power amount ($E_{Target}$) as $TX_L$ elapses, and the power supply amount is decreased as the elapsed puff time becomes longer. For example, the control circuit 50 may apply the magnitude of the power supply output of the puff operation (Boost_L) when the slope absolute value is less than threshold value X, may apply the magnitude of the power supply output of the puff operation (Boost_L1) when the slope absolute value is equal to or larger than threshold value X and less than threshold value Y, and may apply the magnitude of the power supply output of the puff operation (Boost_L2) when the slope absolute value is equal to or larger than threshold value Y.

In the example shown in FIG. 19, although a case is exemplified where the magnitude of the power supply output of the puff operation (Boost_L1) and the puff operation (Boost_L2) is decreased stepwise (discontinuously), the magnitude of the power supply output of the puff operation (Boost_L1) and the puff operation (Boost_L2) may be continuously decreased.

In FIG. 19, although a case is exemplified where the representative value of the required-time samples is larger than the above-described $TX_2$, similar control is also possible for a case where the representative value of the required-time samples is smaller than the above-described $TX_2$.

[Other Embodiments]

Although the present invention has been described with the above-described embodiments, the descriptions and drawings forming a part of the disclosure should not be construed as limiting the present invention. From this disclosure, various alternative embodiments, examples, and operation techniques will be apparent to those skilled in the art.

In the embodiment, the tobacco source 131 has been exemplified as a flavor source. However, the embodiment is not limited to this. The flavor source may not include a tobacco material. Furthermore, the non-combustion type flavor inhaler 100 may not have a flavor source, and the aerosol source may be provided with a flavoring component.

In the embodiment, a case has been exemplified where the non-combustion type flavor inhaler 100 has the capsule unit 130. However, the embodiment is not limited to this. For example, the non-combustion type flavor inhaler 100 may have a cartridge containing a flavor source.

In the embodiment, a case has been exemplified where the puff detection unit 51 detects the start or end of the puff duration when the slope formed by two or more response values output from the sensor 20 has a negative sign, and the slope absolute value having a negative sign is larger than the predetermined value. However, the embodiment is not limited to this. Specifically, the puff detection unit 51 may detect the start or end of the puff duration when the slope formed by two or more response values output from the sensor 20 has a positive sign, and the slope absolute value having a positive sign is larger than the predetermined value. In such a case, the expression "negative" in the embodiment may be replaced with "positive". It should be noted that which of "positive" and "negative" should be applied depends on the type or the like of the sensor 20, namely, the output pattern of the sensor 20 for a user's puff operation.

Although not specifically mentioned in the embodiment, the pushbutton 30 forms a switch member that starts and stops energization from the power source 10 to the control circuit 50 and the sensor 20. Since energization to the sensor 20 is stopped by depression of the pushbutton 30, power consumption can be reduced.

Although not specifically mentioned in the embodiment, before the detection of the start of the puff duration, the sensor 20 may be turned off when the response value monitored at the sampling period Δta does not change over a predetermined period (e.g., 200 msec to 500 msec). This enables power saving. In addition, in such a case, the sensor 20 is preferably turned on when a predetermined time (e.g., 50 msec) has elapsed since the sensor 20 has been turned off. This can ensure the followability of the magnitude of the power supply output to the heat source 80 while achieving power saving. It should be noted that, when the response value monitored at the sampling period Δta changes, the sensor 20 is continuously turned on. In addition, as a behavior different from on/off of the sensor 20, the sensor 20 may repeat on/off in synchronization with the sampling period (Δt) and the calculation cycle of S(n).

Although not specifically mentioned in the embodiment, since the tobacco source 131 is held in the capsule unit 130, it is possible to change the pH of an aqueous solution obtained by adding ten times of weight of water to a tobacco material contained in the tobacco source 131 for each capsule unit 130. In such a case, depending on a type of the capsule unit 130, the gradient of the magnitude of the power supply output to the heat source 80 may be changed along with an increase in the number of puff operations.

Although not specifically mentioned in the embodiment, the number of puff operations may be corrected by a value (aerosol generation amount) defined by the magnitude of the power supply output to the heat source 80 per one puff operation. Specifically, when an amount of aerosol generated by one puff operation is smaller than the predetermined value, the number of puff operations may be accumulated by adding a value in one time multiplied with a predetermined coefficient α (α<1). On the other hand, when the amount of aerosol generated by one puff operation is larger than the predetermined value, the number of puff operations may be accumulated by adding a value in one time multiplied with a predetermined coefficient β (β>1). In other words, the number of puff operations may not necessarily be an integer.

Although not specifically mentioned in the embodiment, in controlling the magnitude of the power supply output in a puff operation series, a timing of increasing the magnitude of the power supply output to the heat source 80 is preferably synchronized with a timing of changing the second light-emitting mode. For example, as shown in FIGS. 8 to 9, when the magnitude of the power supply output to the heat source 80 increases between puff states #4 and #5, the second light-emitting mode is preferably changed between puff states #4 and #5.

Although not specifically mentioned in the embodiment, as shown in FIGS. 10 and 11, while a voltage smaller than a standard voltage is applied to the heat source 80 in the duration after the first duration T1 or the third duration T3 elapses, the first light-emitting mode is preferably continued even in such a section.

In the embodiment, there are provided the first mode (Low mode shown in FIG. 8) that uses the magnitude of the first reference power supply output as the magnitude of the reference power supply output, and the second mode (High mode shown in FIG. 9) that uses the magnitude of the second reference power supply output larger than the magnitude of the first reference power supply output, as the magnitude of the reference power supply output. In such a case, the light-emitting mode in the first mode may be different from the light-emitting mode in the second mode. Namely, the first light-emitting mode, the second light-emitting mode, and the ending light-emitting mode in the first mode may be respectively different from the first light-emitting mode, the second light-emitting mode, and the ending light-emitting mode in the second mode.

Although not specifically mentioned in the embodiment, there may be provided a program that causes a computer to execute each process to be performed by the non-combustion type flavor inhaler 100. Further, the program may be stored in a computer readable medium. Using a computer readable medium enables installation of a program in a computer. Here, the computer readable medium stored with the program may be a non-transitory recording medium. The non-transitory recording medium is not particularly limited, but it may be a recording medium such as a CD-ROM or a DVD-ROM, for example.

Alternatively, there may be provided a chip configured by a memory that stores a program for executing each process to be performed by the non-combustion type flavor inhaler 100, and a processor that executes a program stored in the memory.

The whole contents of Japanese Patent Application No. 2014-095164 (filed May 2, 2014) is incorporated herein by reference.

INDUSTRIAL APPLICABILITY

According to the embodiment, it is possible to provide the non-combustion type flavor inhaler that can appropriately and quickly control a total amount of aerosol to be inhaled by a user for each puff operation.

The invention claimed is:
1. A non-combustion type flavor inhaler comprising:
a housing having an airflow path continuing from an inlet to an outlet;
an atomizing part that atomizes an aerosol source without burning;
a sensor outputting a value that changes according to a user's puff operation; and
a control unit that controls a power supply output to the atomizing part based on an absolute value of a slope formed by a change in a value output from the sensor over time such that an aerosol amount falls within a desired range, wherein the aerosol amount is an amount of an aerosol to be atomized by the atomizing part in one energization to the atomizing part, and wherein the control unit increases the magnitude of the power supply output to the atomizing part as the absolute value of the slope is larger.

2. The non-combustion type flavor inhaler according to claim 1, wherein the control unit reduces the magnitude of the power supply output to the atomizing part as an elapsed time from a start of energization to the atomizing part in one energization to the atomizing part is increased.

3. The non-combustion type flavor inhaler according to claim 1, wherein when a supply duration has elapsed since energization to the atomizing part has been started, the control unit stops the energization to the atomizing part such that the aerosol amount falls within the desired range and wherein the control unit determines the supply duration based on a learning result of required time of a user's puff operation.

4. The non-combustion type flavor inhaler according to claim 1, wherein the control unit uses a predetermined magnitude as the magnitude of the power supply output to the atomizing part when the absolute value of the slope is within a predetermined range, and wherein the control unit increases the magnitude of the power supply output to the atomizing part to be larger than the predetermined magnitude when the absolute value of the slope is larger than the predetermined range.

5. The non-combustion type flavor inhaler according to claim 1, wherein an increase rate of the magnitude of the power supply output to the atomizing part is greater than 1 and equal to or less than 3.

6. The non-combustion type flavor inhaler according to claim 1, wherein when a supply duration has elapsed since energization to the atomizing part has been started, the control unit stops the energization to the atomizing part such that the aerosol amount falls within the desired range, and wherein the supply duration is equal to or less than an upper limit value of a standard puff period derived from statistics of a puff period of a user.

7. The non-combustion type flavor inhaler according to claim 6, wherein the control unit reduces the supply duration as the absolute value of the slope increases.

8. The non-combustion type flavor inhaler according to claim 6, wherein the control unit uses a predetermined duration as the supply duration when the absolute value of the slope is within a predetermined range, and wherein the control unit reduces the supply duration to be shorter than the predetermined duration when the absolute value of the slope is greater than the predetermined range.

9. The non-combustion type flavor inhaler according to claim 7, wherein a reduction rate of the supply duration is equal to or greater than ⅓ and less than 1.

10. The non-combustion type flavor inhaler according to claim 6, wherein in a first puff operation in which the absolute value of the slope is a first slope absolute value, the magnitude of the power supply output to the atomizing part is represented by $PX_1$, and the supply duration is represented by $TX_1$;

in a second puff operation in which the absolute value of the slope is a second slope absolute value larger than the first slope absolute value, the magnitude of the power supply output to the atomizing part is represented by $PX_2$, and the supply duration is represented by $TX_2$; and the $TX_2$ is calculated according to an expression of $TX_2 = (PX_1/PX_2) \times TX_1$.

* * * * *